(12) United States Patent
Merboth et al.

(10) Patent No.: US 8,413,810 B2
(45) Date of Patent: Apr. 9, 2013

(54) PACKAGES FOR MEDICAL DEVICES AND METHODS THEREFOR

(75) Inventors: Barbara L. Merboth, Bridgewater, NJ (US); Raymond Parker, New Hope, PA (US); Mehmet Reyhan, East Windsor, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 12/882,619

(22) Filed: Sep. 15, 2010

(65) Prior Publication Data
US 2012/0061262 A1 Mar. 15, 2012

(51) Int. Cl.
*A61B 19/02* (2006.01)
*B65D 81/26* (2006.01)
*B65D 85/00* (2006.01)

(52) U.S. Cl.
USPC ............ 206/363; 206/438; 206/204; 206/484

(58) Field of Classification Search .................. 206/363, 206/570, 370, 438, 210, 484, 440, 204
See application file for complete search history.

(56) References Cited

U.S. PATENT DOCUMENTS

| | | | |
|---|---|---|---|
| 3,724,651 A | 4/1973 | Link | |
| 3,926,309 A | 12/1975 | Center | |
| 4,206,844 A * | 6/1980 | Thukamoto et al. | 206/439 |
| 4,511,035 A * | 4/1985 | Alpern | 206/363 |
| D282,482 S | 2/1986 | Anderson | |
| D282,684 S | 2/1986 | Cline | |
| 4,844,251 A * | 7/1989 | Gueret | 206/222 |
| 5,031,775 A | 7/1991 | Kane | |
| 5,106,662 A | 4/1992 | Khayat | |
| 5,226,535 A * | 7/1993 | Rosdhy et al. | 206/363 |
| 5,234,106 A * | 8/1993 | Transue et al. | 206/363 |
| 5,358,624 A * | 10/1994 | Roshdy et al. | 206/363 |
| D356,677 S | 3/1995 | Kalasountas | |
| 5,447,231 A | 9/1995 | Kastenhofer | |
| 5,487,469 A * | 1/1996 | Roshdy et al. | 206/363 |
| 5,497,601 A * | 3/1996 | Gonzalez | 53/449 |

(Continued)

FOREIGN PATENT DOCUMENTS

| | | |
|---|---|---|
| EP | 0440427 | 6/1994 |
| EP | 0664991 | 8/1995 |
| WO | 2008033874 | 3/2008 |

OTHER PUBLICATIONS

International Search Report for International Application No. PCT/US2011/051285 mailed Dec. 27, 2011, 5pp.

*Primary Examiner* — Steven A. Reynolds
(74) *Attorney, Agent, or Firm* — Doherty & Charney LLC

(57) ABSTRACT

A package for a medical device having a handle and an elongated shaft. The package includes a holster for holding the medical device, the holster having a tubular member for receiving the elongated shaft and a handle cover located at a proximal end thereof. The handle cover has a holster opening for accessing the handle to draw the medical device from the holster. The package includes a pouch having a sealed area bounded by a top sealed edge, a bottom sealed edge, a pair of side sealed edges extending between the top and bottom sealed edges, and at least one opening tab spaced from the bottom sealed edge. The medical device and the holster are disposed within the sealed area of the pouch with the elongated shaft of the medical device extending along the bottom sealed edge and the holster opening being located adjacent the at least one opening tab.

19 Claims, 21 Drawing Sheets

U.S. PATENT DOCUMENTS

| | | | | |
|---|---|---|---|---|
| 5,501,341 A | * | 3/1996 | Van Es | 206/364 |
| 5,601,189 A | * | 2/1997 | Roshdy | 206/363 |
| 5,655,657 A | | 8/1997 | Roshdy | |
| 5,699,909 A | * | 12/1997 | Foster | 206/370 |
| D395,359 S | | 6/1998 | Olsen | |
| 5,788,063 A | * | 8/1998 | Van Ness | 206/63.3 |
| 5,842,567 A | | 12/1998 | Rowe | |
| 5,878,549 A | | 3/1999 | Littman et al. | |
| D411,948 S | | 7/1999 | Chipperfield | |
| 6,308,875 B1 | | 10/2001 | Almo | |
| 6,986,730 B1 | * | 1/2006 | Hoekstra | 493/224 |
| D541,933 S | | 5/2007 | White et al. | |
| D542,525 S | | 5/2007 | Schmidt | |
| 7,247,329 B2 | * | 7/2007 | Mattisson | 426/108 |
| D562,549 S | | 2/2008 | Bodnar | |
| D576,275 S | | 9/2008 | White et al. | |
| D578,642 S | | 10/2008 | White et al. | |
| D590,246 S | * | 4/2009 | Kirk et al. | D9/732 |
| 2002/0165549 A1 | | 11/2002 | Owusu-Akyaw | |
| 2005/0092636 A1 | * | 5/2005 | Su-Syin | 206/363 |
| 2005/0189252 A1 | * | 9/2005 | Naylor et al. | 206/439 |
| 2010/0292710 A1 | | 11/2010 | Daniel et al. | |
| 2010/0292712 A1 | | 11/2010 | Nering et al. | |
| 2010/0292713 A1 | | 11/2010 | Cohn et al. | |
| 2010/0292715 A1 | | 11/2010 | Nering et al. | |

\* cited by examiner

PACKAGES FOR MEDICAL DEVICES AND METHODS THEREFOR

BACKGROUND OF THE INVENTION

1. Field of the Invention

The present invention generally relates to medical devices and more particularly relates to packages for medical devices and methods therefor.

2. Description of the Related Art

During surgical procedures, great care is taken to prevent contamination of the surgical tools and medical devices used during the course of an operation. An operating team typically includes at least one member whose function is to open packages containing surgical tools and medical devices and to present them to a sterile nurse or surgeon in a manner whereby they remain in a sterile condition.

There have been many efforts directed to providing packages for medical devices that allow for efficient opening of the package and presentation of the medical devices to surgical personnel in a sterile condition. One type of package provides a color-marked envelope that indicates the area to be torn off to provide an access opening to the contents within the envelope without affecting the sterility of the contents. Another type of package provides a tear string that may be pulled to open the envelope so that the contents may be removed using forceps or another similar tool.

Packages for medical devices have also been provided having integral tear strips, which, when removed, not only sever the packages but provide delaminated margins on the exterior surfaces of the packages adjacent to the severed edges. It has been found that great care must be taken in the removal of the tear strip to avoid failure of the strip before the de-lamination is completed and the package is completely open. While a sterile surface area adjacent to the access area is provided by this method, the sterile area is limited in width to the delaminated margin which, of necessity, must be narrowed to prevent failure of the tear strip. Accordingly, the degree of care required in removing the contents of the package without contacting an unsterile surface surrounding the access area is, while lessened, still significant.

Commonly assigned U.S. Pat. No. 3,724,651 to Link discloses a peelable package for containing surgical tools and medical devices that may be sealed and sterilized within the package and subsequently removed therefrom with a minimum probability of contamination by the unsterile outer surfaces of the package. The package has two panels sealed together at their marginal portions to form a chamber therebetween having a sealed mouth and adjacent sealed edges. A section of the sealed marginal portions of one panel, extending across the mouth and along the adjacent edges of the package, is weakened, by scoring, so that upon opening the package, the weakened section of the panel will delaminate to the depth of the scoring in preference to yielding at the seal. The package is also provided with tabs extending beyond a sealed mouth. The tabs include bending scores which allow them to be folded away from the sterile portions of the package and additionally initiate the delamination of the panel when opening the package.

U.S. Pat. No. 5,878,549 to Littman et al. discloses an easy open tear control package, such as a pouch, made from a film of polymeric barrier material. The easy open tear control feature is formed from roughening portions of the outer and inner surface of the films, prior to fabricating the films into a package. The roughened portion is on one face or on each face of the package and is at least a full width of the seal when the film is made into the package. The roughened portion can extend the entire width of the package and can be of any desired length. With the package disclosed in the '549 patent, it is difficult to rapidly remove the contents of the package while maintaining sterility.

In spite of the above advances, there remains a need for an improved package for medical devices that is easy to open and that insures the contents inside the package are maintained in a sterile environment. In addition, there remains a need for an improved package, such as a foil pouch, that may be easily opened in a surgical environment for efficiently presenting medical devices or tools to surgical personnel. There also remains a need for a package that provides a clear indication of the end of the package that is to be opened for efficiently accessing the medical devices for use during a surgical procedure. Moreover, there remains a need for a package that facilitates loading a medical device inside the package, as well as a need for improved methods for packaging medical devices and tools.

SUMMARY OF THE INVENTION

In one embodiment, a package for a medical device preferably includes a medical device, such as an implant applicator gun, having a handle and an elongated shaft projecting from the handle, and a holster for holding the medical device, the holster including a tubular member that extends to a distal end thereof for receiving the elongated shaft and a handle cover located at a proximal end thereof that receives the handle. The handle cover desirably has a holster opening for accessing the handle to draw the medical device from the proximal end of the holster for use during a surgical procedure. The holster may be made of paper that is adapted to absorb moisture present inside the pouch. In one embodiment, the holster may include a solid bleach sulfate (SBS) material.

In one embodiment, the package desirably includes a pouch having a sealed area bounded by a top sealed edge, a bottom sealed edge, and a pair of side sealed edges extending between the top and bottom sealed edges. The pouch desirably includes at least one opening tab spaced from the bottom sealed edge. The pouches are desirable manufactured and sealed in a sterile environment. In one embodiment, the medical device and the holster are preferably disposed within the enclosed area of the sealed pouch with the elongated shaft of the medical device extending along the bottom sealed edge and the holster opening being located adjacent the at least one opening tab.

In one embodiment, the handle and the handle cover preferably extend away from the bottom sealed edge toward the at least one opening tab. The at least one opening tab is desirably closer to the holster opening than the distal end of the holster.

In one embodiment, the holster includes a foldable blank having a first blank half, a second blank half, and a center fold line extending between the first and second blank halves. The first blank half preferably includes a first handle cover section adjacent the proximal end of the holster and a first shaft cover extending between the first handle cover section and the distal end of the holster. The second blank half preferably includes a second handle cover section adjacent the proximal end of the holster and a second shaft cover extending between the second handle cover section and the distal end of the holster. In one embodiment, the second blank half is foldable along the center fold line for covering the first blank half.

In one embodiment, the foldable blank desirably includes a stop tab projecting from a distal edge of the first handle cover section. A locking slit may be formed in the second handle cover section, whereby the stop tab is adapted to engage the locking slit for coupling distal edges of the first and second handle cover sections together. In one embodiment, the stop tab is adapted to stop movement of the medical device toward the distal end of the holster when the medical device is inserted into the holster, which preferably prevents the medical device from shifting around within the pouch when sealed therein.

In one embodiment, the holster desirably includes a distal tab projecting from a distal end of the first shaft cover. The distal tab is preferably foldable over a distal end of the elongated shaft of the medical device when the medical device is positioned over the blank.

In one embodiment, the second shaft cover desirably has a score line that extends along the length of the second shaft cover for bisecting the second shaft cover into a first foldable part and a second foldable part. The second shaft cover may have a cut line that intersects with a proximal end of the score line for enabling the first foldable part to be folded over the second foldable part along the score line.

In one embodiment, the first foldable part is foldable over the second foldable part which, in turn, is foldable over the first shaft cover for forming the tubular member. The distal tab may be positioned between the first foldable part and the second foldable part for covering a distal end of the tubular member and a distal end of the medical device shaft.

In one embodiment, the pouch preferably includes a foil pouch including first and second foil sheets that are sealed together by a continuous seal including the upper sealed edge, the bottom sealed edge and the pair of side sealed edges. The at least one opening tab desirably includes a first pull tab connected with the first foil sheet and a second pull tab connected with the second foil sheet. The first and second pull tabs are preferably peelable away from one another for breaking the continuous seal to open the pouch for accessing the medical device through the holster opening.

In one embodiment, the pouch has a rectangular shape and the top and bottom sealed edges extend along the length of the sealed pouch. In one embodiment, the at least one opening tab is desirably spaced from the bottom sealed edge and is located in a first corner of the rectangular pouch that is diagonally opposite from a second corner of the rectangular pouch that is adjacent a distal end of the elongated shaft.

In one embodiment, a package for a medical device preferably includes a medical device including a handle at a proximal end and an elongated shaft that extends toward a distal end of the medical device, and a holster adapted to receive and hold the medical device, the holster including a tubular member that receives the elongated shaft and a handle cover that at least partially covers the handle, the handle cover having a holster opening for accessing the handle and drawing the medical device from the holster. The package may include a rectangular shaped sealed pouch having a bottom sealed edge, a top sealed edge, a pair of side sealed edges that extend between the top and bottom sealed edges, and at least one opening tab spaced from the bottom sealed edge. The medical device and the holster containing the medical device are desirably positioned within an enclosed area of the sealed pouch so that the elongated shaft extends along the bottom sealed edge and the holster opening is adjacent the at least one opening tab, whereby the at least one opening tab is spaced from the bottom sealed edge and is diagonally opposite from a distal end of the medical device shaft.

In one embodiment, a method of delivering a sterile medical device to surgical personnel desirably includes providing a medical device including a handle and a shaft projecting distally from the handle, and wrapping a holster around the medical device, the holster including a tubular member covering the medical device shaft and a handle cover at least partially covering the medical device handle, the handle cover having a holster opening for accessing the handle. The method desirably includes providing a pouch including a top sealed edge, a bottom sealed edge, a first side sealed edge extending between the top and bottom sealed edges, at least one opening tab located between the top sealed edge and the first side sealed edge, and a second side including a pouch opening opposite the first side sealed edge.

In one embodiment, a method includes inserting the medical device through the pouch opening and into the pouch so that the handle is adjacent the first side sealed edge and the medical device shaft extends along the bottom sealed edge. After inserting the medical device, the medical device and the holster are preferably sterilized and the pouch is desirably closed by sealing the second side of the pouch to form a second side sealed edge.

In order to open the pouch, the method may include pulling the at least one opening tab for opening the pouch, reaching through a pouch opening and into the holster opening for accessing the handle of the medical device, and drawing the medical device from the holster and removing the medical device from the pouch.

In one embodiment, the method desirably includes using a first person for pulling the at least one opening tab for opening the pouch, and using a second person in a sterile environment for reaching through the pouch opening and into the holster opening for drawing the medical device from the holster and removing the medical device from the pouch.

In one embodiment, a medical device is placed on the paper blank and the blank is wrapped around the device to form the holster without the need to lift or shift the device. The device in the paper holster is placed handle end first into the pouch through the Tyvek® end. The Tyvek end is sealed and the assembly is sterilized and dried with the stainless steel shaft extending along the base of the foil pouch to minimize shifting during transportation and eliminate the need to tack the foil pouch or attach the holster to the foil pouch. The final foil seal is placed at the distal tip of the elongated shaft of the medical device. Using this loading and sealing protocol enables a shorter pouch length to be used since the flat seal area distance from the distal tip of the medical device (a three dimensional component) to the final seal (a two dimensional component) is minimized. If the larger three dimensional handle was nearest to the final seal, the flat seal area would have to be located at a greater distance from the medical device which would require a longer pouch.

In one embodiment, upon peeling open the foil pouch, the paper holster springs open, thereby pushing the foil sheets of the foil pouch apart for creating a holster opening that allows sterile retrieval of the medical device. The design of the holster enables a sterile tech to put his or her hand inside the pouch and inside the holster opening of the paper holster for removing the medical device, such as an implant applicator gun. This shape, size and configuration of the paper holster relative to the foil pouch enables the paper holster to remain inside the foil pouch during withdrawal of the medical device without the need to secure or tack the paper folder to the foil pouch.

In one embodiment, the present invention is directed to packaging for medical devices. It should be clearly understood that, however, that the present invention is not limited thereto and may be embodied in any packaging requirement wherein the features of rapid opening and easy removal of the package contents are desirable These and other preferred embodiments of the present invention will be described in more detail below.

DETAILED DESCRIPTION

Figure 1:
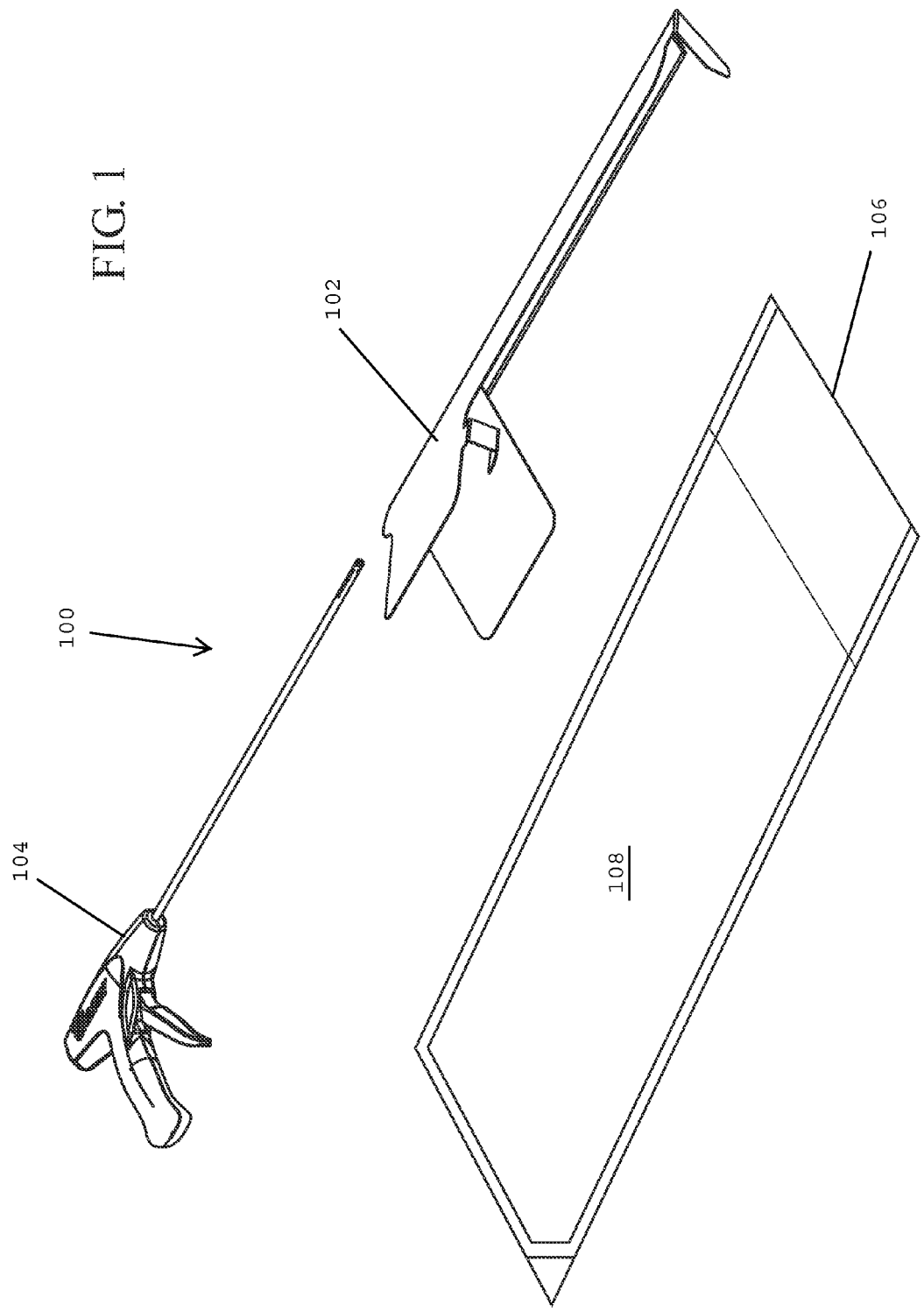
FIG. 1 shows a perspective view of a package for a medical device including the medical device, a holster adapted to receive the medical device, and a pouch adapted to receive the holster and the medical device, in accordance one embodiment of the present invention.

Referring to FIG. 1, in one embodiment, a package 100 for a medical device desirably includes a holster 102 adapted to receive a medical device 104. After the medical device 104 has been positioned inside the holster 102, the holster/medical device subassembly is preferably insertable into an opening 106 of a sealable pouch 108 and the opening 106 may be sealed, as will be described in more detail herein.

Figure 2:
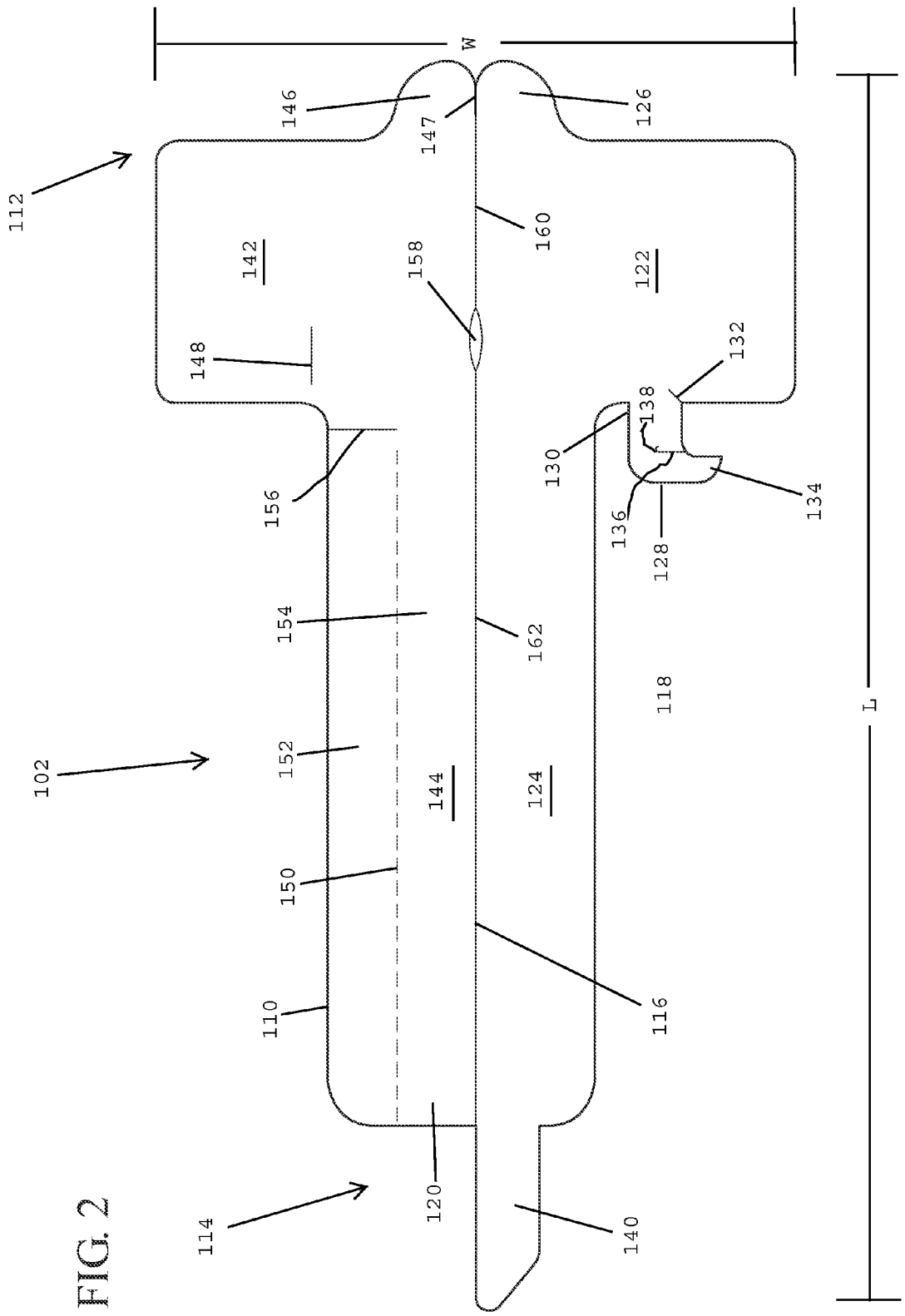
FIG. 2 shows a top plan view of the holster of FIG. 1 in an unfolded configuration, in accordance with one embodiment of the present invention.

Referring to FIG. 2, in one embodiment, the holster 102 is preferably formed from a foldable blank 110 that is adapted to be wrapped around a medical device. In one embodiment, the foldable blank 110 is made of paper, which is adapted to remove moisture from the inside of a sealed pouch. Although the present invention is not limited by any particular theory of operation, it is believed that any moisture present within the package will be absorbed by the paper material of the holster rather than contacting the medical device. In one embodiment, the paper blank 110 may be made of a solid bleach sulfate (SBS) material, such as a nine point SBS sheet.

In one embodiment, the paper blank 110 preferably has a proximal end 112 and a distal end 114. The paper blank 110 desirably includes a center fold line 116 that extends along a longitudinal axis between the proximal end 112 and the distal end 114 thereof. The center fold line 116 preferably divides the paper blank 110 into a first half 118 of the holster and a second half 120 of the holster that is adapted to be folded over the first half 118. In one embodiment, the blank 110 preferably has a length L of about 20-25 inches, and a width W of about 10-15 inches. In one embodiment, the paper blank 110 has a weight of between about 15-20 grams and more preferably about 16.5 grams.

In one embodiment, the first half 118 of the blank preferably includes a first handle cover section 122 and a first shaft cover 124. A first proximal end tab 126 preferably projects from a proximal edge of the first handle cover section 122, and a laterally extending stop 128 preferably projects from a distal edge of the first handle cover section 122. In one embodiment, the stop tab 128 desirably includes a first section 130 that is connected with the distal edge of the first handle cover 122 section. An angled cut line 132 is formed in the first handle cover section 122 that is adjacent a proximal end of the first section 130. The stop tab 128 also desirably includes a hook 134 that extends from a distal end of the first section 130 of the stop tab 128. A second vertically extending cut line 136 is formed between the hook 134 and the first tab section 130. The second cut line 136 has an inner end 138 that preferably defines a curved radius.

In one embodiment, the paper blank 110 also desirably includes a distal tab 140 that extends from a distal end of the first shaft cover 124. The distal tab 140 is foldable over the distal end of the first shaft cover 124 for preferably covering a distal end of a medical device such as an opening at the distal end of an elongated shaft of a medical device.

In one embodiment, the second half 120 of the paper blank 110 preferably includes a second handle cover section 142 and a second shaft cover 144 that extends to the distal end 114 of the paper blank. The paper blank 110 desirably includes a second proximal tab 146 that extends from a proximal edge of the second handle cover section 142. The blank 110 preferably includes a proximal end cut line 147 that extends between the first and second proximal end tabs 126, 146 that enables the first and second proximal end tabs to be folded over one another. The second handle cover section 142 also preferably includes a locking slot 148 formed therein that is adapted to receive the hook 134 of the stop tab 128 when the second handle cover section 142 is folded over the first handle cover section 122.

In one embodiment, when the stop tab 128 is inserted into the locking slot 148, the proximal edges of the first and second handle cover sections 122, 142 are preferably closer together than the respective distal edges of the first and second handle cover sections 122, 142 for providing a relatively wide holster opening for accessing a medical device as will be described in more detail herein.

In one embodiment, the second shaft cover 144 preferably includes a score line 150 that divides the second shaft cover 144 into a first foldable part 152 and a second foldable part 154. The score line 150 preferably extends from a distal end 114 of the second shaft cover 144 to a cut line 156 formed in the paper blank 100 adjacent a distal edge of the second handle cover section 142. The score line 150 and the cut line 156 desirably enable the first foldable part 152 to be folded over the second foldable part 154 for forming a tubular member that is adapted to receive an elongated shaft of a medical device.

In one embodiment, the center fold line 116 extends between the proximal end 112 and the distal end 114 of the foldable paper blank 110. The center fold line 116 defines a single line for most of the length thereof that splits into two curved lines defining an oval shaped section 158. The oval-shaped section 158 is preferably positioned between the first and second handle cover sections 122, 142. In one embodiment, the oval-shaped section 158 is located proximally from the distal edges of the first and second handle cover sections 122, 142. In one embodiment, the oval-shaped section 158 is located along the center fold line 116 between the stop tab 128 and the first and second proximal end tabs 126, 146.

In one embodiment, the center fold line 116 desirably includes a first section 160 defining a single line that extends from the proximal end 112 of the blank 110 toward the oval-shaped section 158. The center fold line 116 desirably includes a second section 162 defining a second single line that extends between a distal end of the oval-shaped section 158 and the distal end 114 of the blank 110.

The oval-shaped section 158 of the blank 110 desirably prevents the second handle cover section 142 from being completely folded over the first handle cover section 122. As a result, the first and second handle cover sections 122, 142 may be urged toward one another when inserted into a pouch, however, the oval-shaped section 158 will cause the first and section handle cover sections 122, 142 to spring away from one another when the pouch is opened for pushing the walls of the opened pouch away from one another.

In one embodiment, the medical device holster 102 is formed from the paper blank 110 that is pre-folded at particular locations before receiving a medical device. In one embodiment, the paper blank 110 is folded in half along the center fold line 116 by folding the second half 120 of the blank, including the second handle cover section 142 and the second shaft cover 144, over the first half 118 of the blank, including the first handle cover section 122 and the first shaft cover 124. The first and second proximal tabs 126, 146 are desirably at least partially folded over the respective first and second handle cover sections 122, 142. The stop tab 128 is preferably at least partially folded over the first handle cover section 122, and the distal tab 140 is folded over the distal end of the first shaft cover 124. In one embodiment, the first foldable part 152 of the second shaft cover 144 is folded over the second foldable part 154 of the second shaft cover. Although the present invention is not limited by any particular theory of operation, it is believed that pre-folding one or more of the tabs and/or sections of the paper blank 110 will facilitate more efficient formation of the holster and more efficient and sanitary wrapping of the medical device inside the medical device holster 102.

Figure 3:
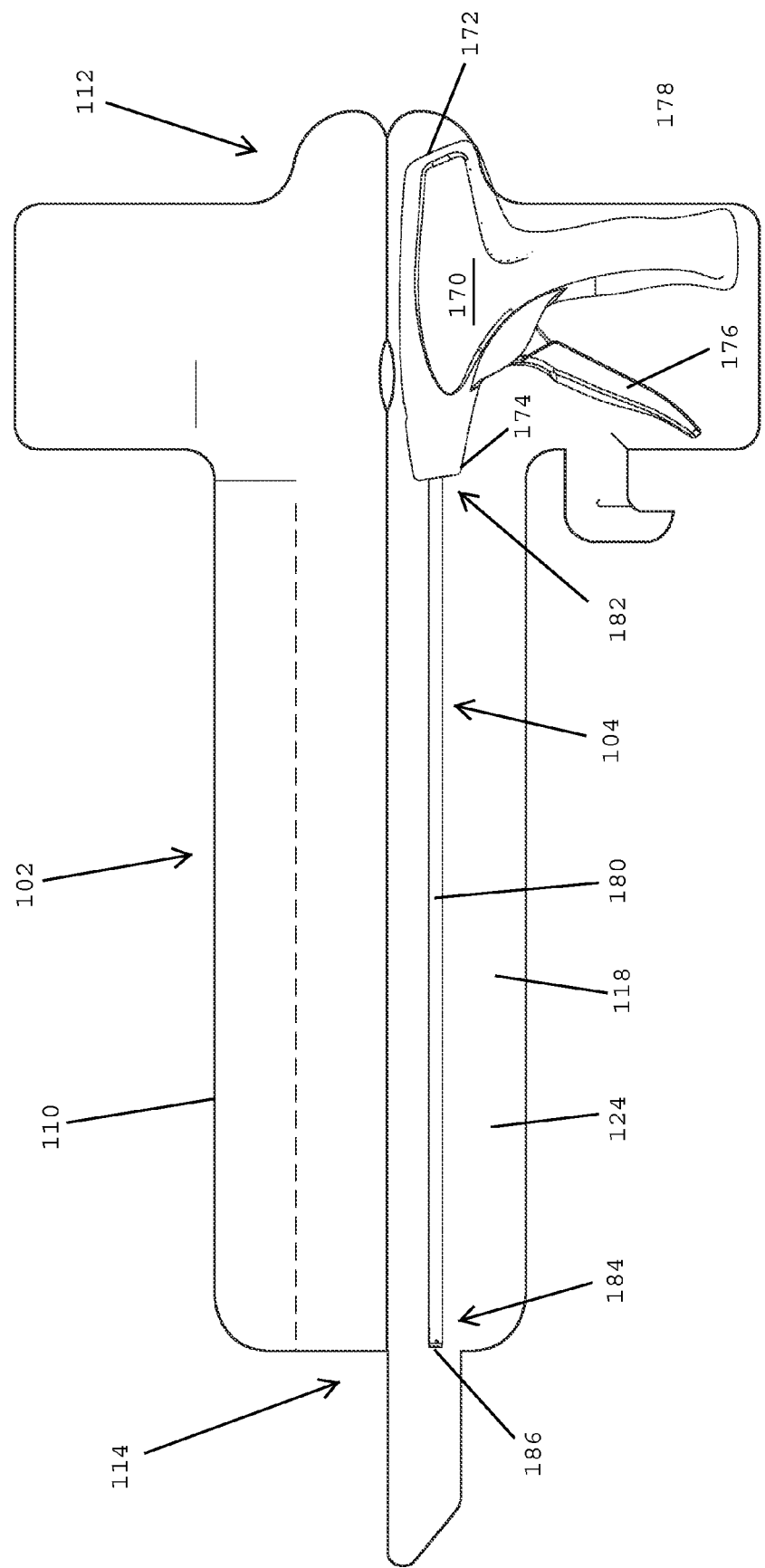
FIGS. 3-10 show a method of wrapping the holster of FIG. 2 around the medical device shown in FIG. 1, in accordance with one embodiment of the present invention.

Referring to FIG. 3, in one embodiment, a medical device 104 is positioned over the first half 118 of the paper blank 110. The medical device 104 desirably includes a handle 170 having a proximal end 172 and a distal end 174, a trigger 176 coupled with the handle 170, and a hand grip 178. The medical device 104 also desirably includes an elongated shaft 180 having a proximal end 182 projecting from a distal end 174 of the handle 170, and a distal end 184 having an opening 186 for dispensing implants. In one embodiment, the elongated shaft is preferably a stainless steel shaft having a central conduit for delivering fasteners from a distal end opening of the shaft. In one embodiment, the medical device 104 preferably incorporates one or more features of the devices disclosed in commonly assigned U.S. patent application Ser. Nos. 12/464,143; 12/464,151; 12/464,165; and 12/464,177, the disclosures of which are hereby incorporated by reference herein.

In one embodiment, after the medical device 104 has been prepared for being wrapped inside the medical device holster 102, the handle 170 of the medical device is positioned over the first handle cover section 122 and the elongated shaft 180 of the medical device is positioned over the first shaft cover 124 so that the handle 170 is adjacent the proximal end 112 of the blank 110 and the distal end 184 of the elongated shaft 180 is located adjacent the distal end 114 of the blank 110.

Figure 4:
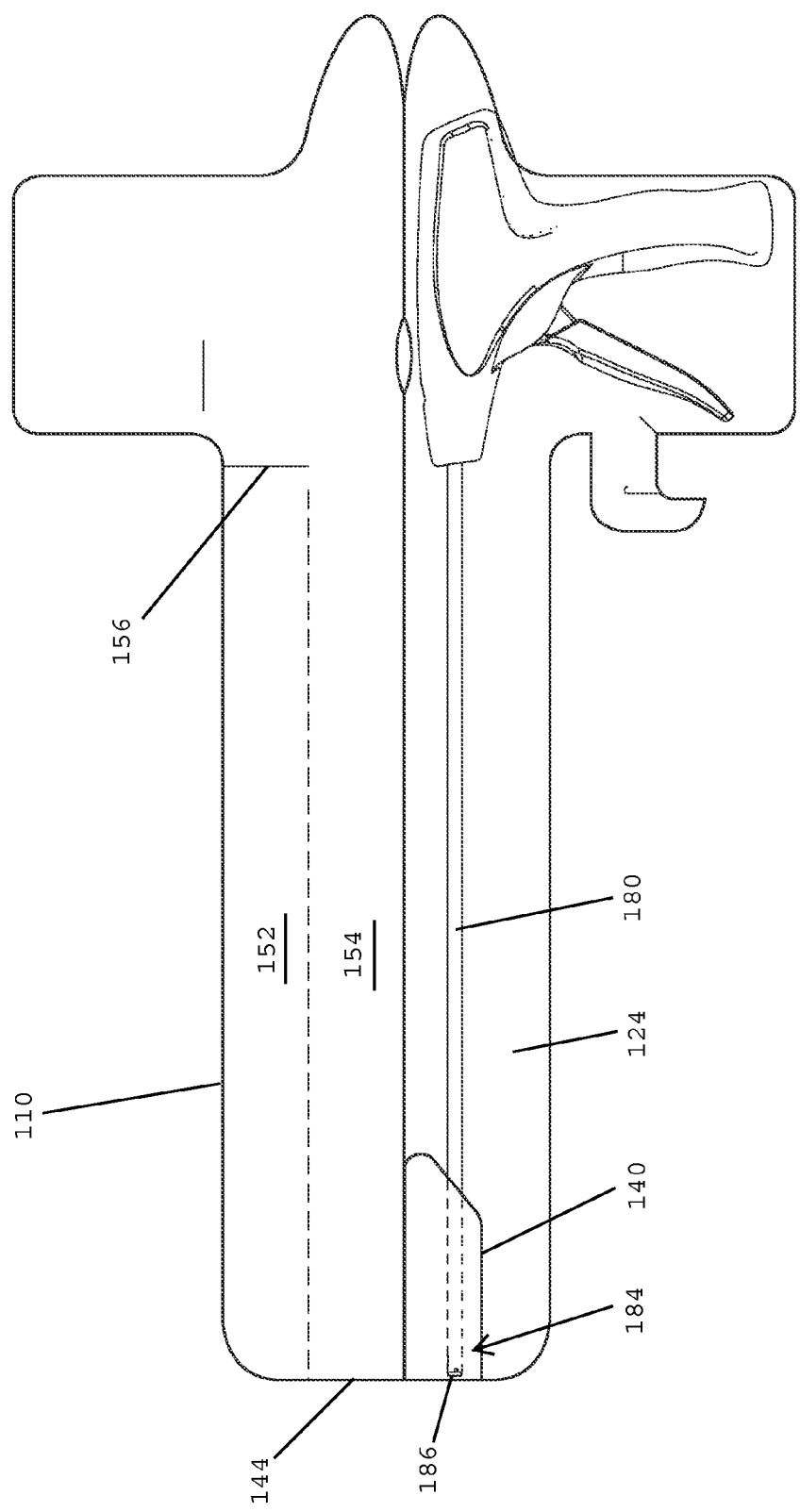
Figure 5:
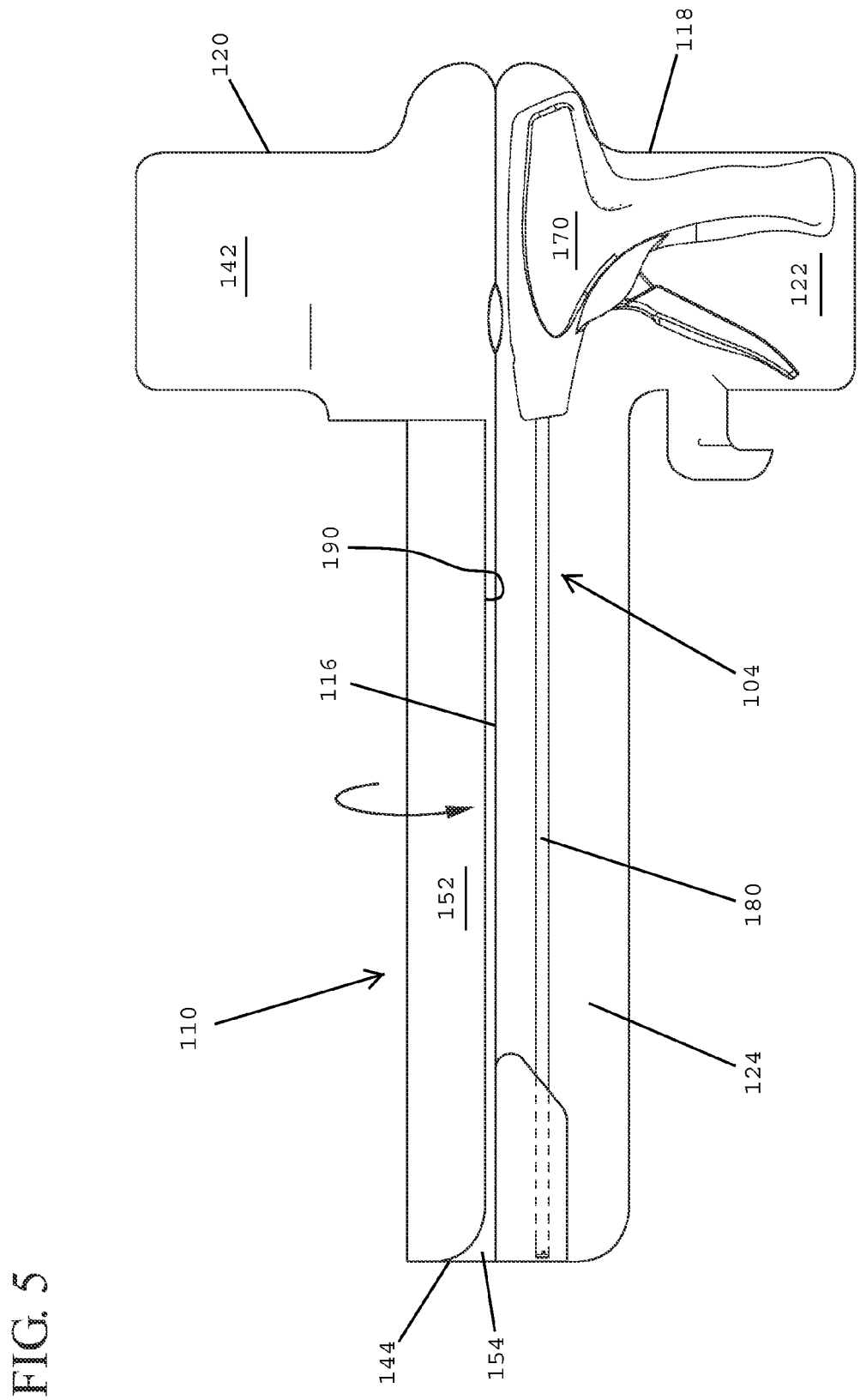

Referring to FIG. 4, in one embodiment, the distal tab 140 of the blank 110 is folded over the distal end 184 of the elongated shaft 180 for covering the opening 186 at the distal end 184 of the shaft 180 and a distal end of the first shaft cover 124. Referring to FIGS. 4 and 5, in one embodiment, the first foldable part 152 of the second shaft cover 144 is folded over the second foldable part 154 of the second shaft cover.

Figure 6:
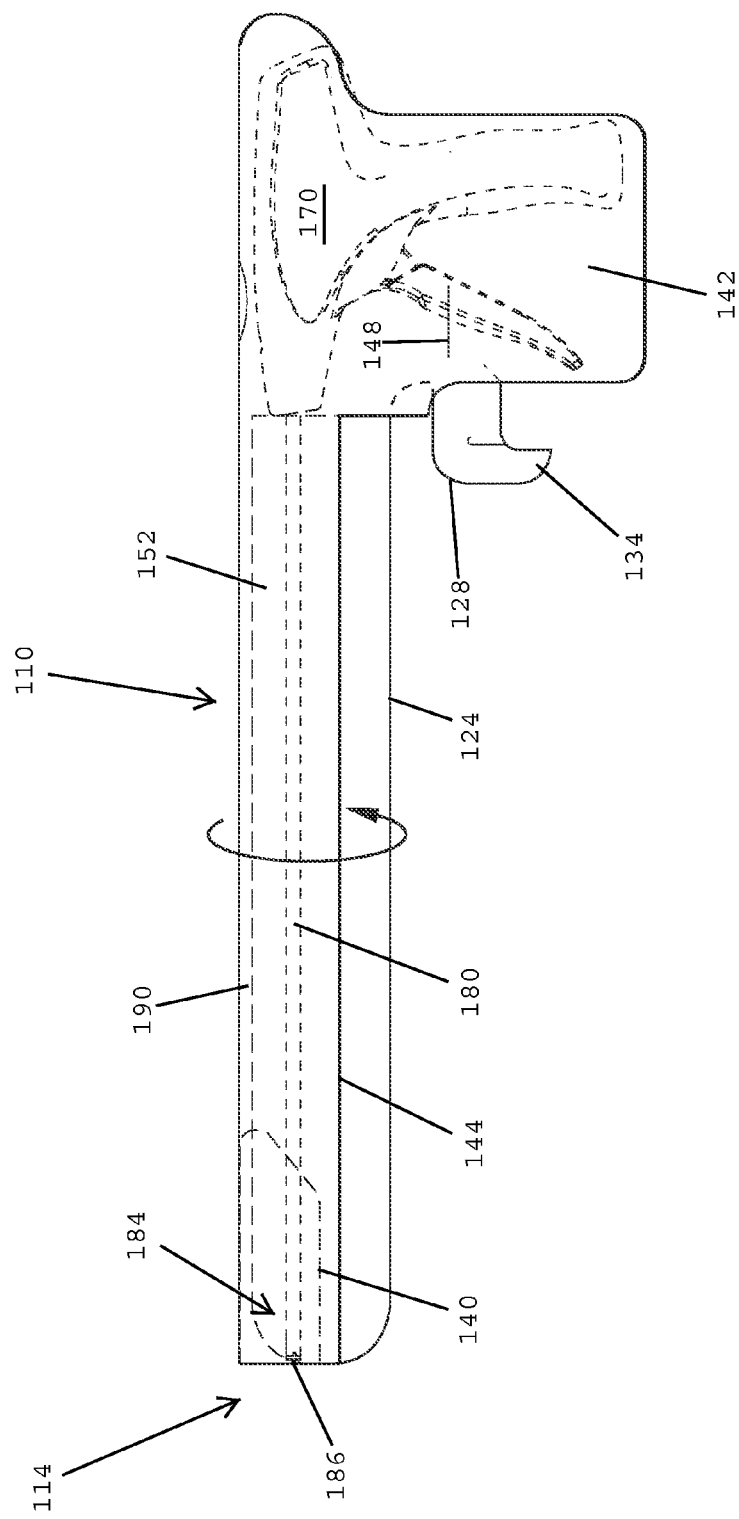

Referring to FIGS. 5 and 6, in one embodiment, the second half 120 of the blank 110 is folded over the first half 118 of the blank. In one embodiment, the second handle cover section 142 and the second shaft cover 144 are folded about the center fold line 116 for covering the handle 170, the first handle cover section 122, and the elongated shaft 180, and the first shaft cover 124.

In one embodiment, the outer edge 190 of the first foldable part 152 of the second shaft cover 144 is preferably tucked under both the elongated shaft 180 of the medical device and the folded-over distal tab 140 to form a tubular-shaped member that wraps around the elongated shaft 180. The folded-over distal tab 140 preferably covers the opening 186 at the distal end 184 of the elongated shaft for preventing the medical device 104 from shifting toward the distal end 114 of the blank 110. In addition, the distal tab 140, which may be made of paper, also absorbs any moisture present within a sealed package so as to minimize contact between the moisture and the medical device or fasteners dispensed from the medical device.

Figure 7:
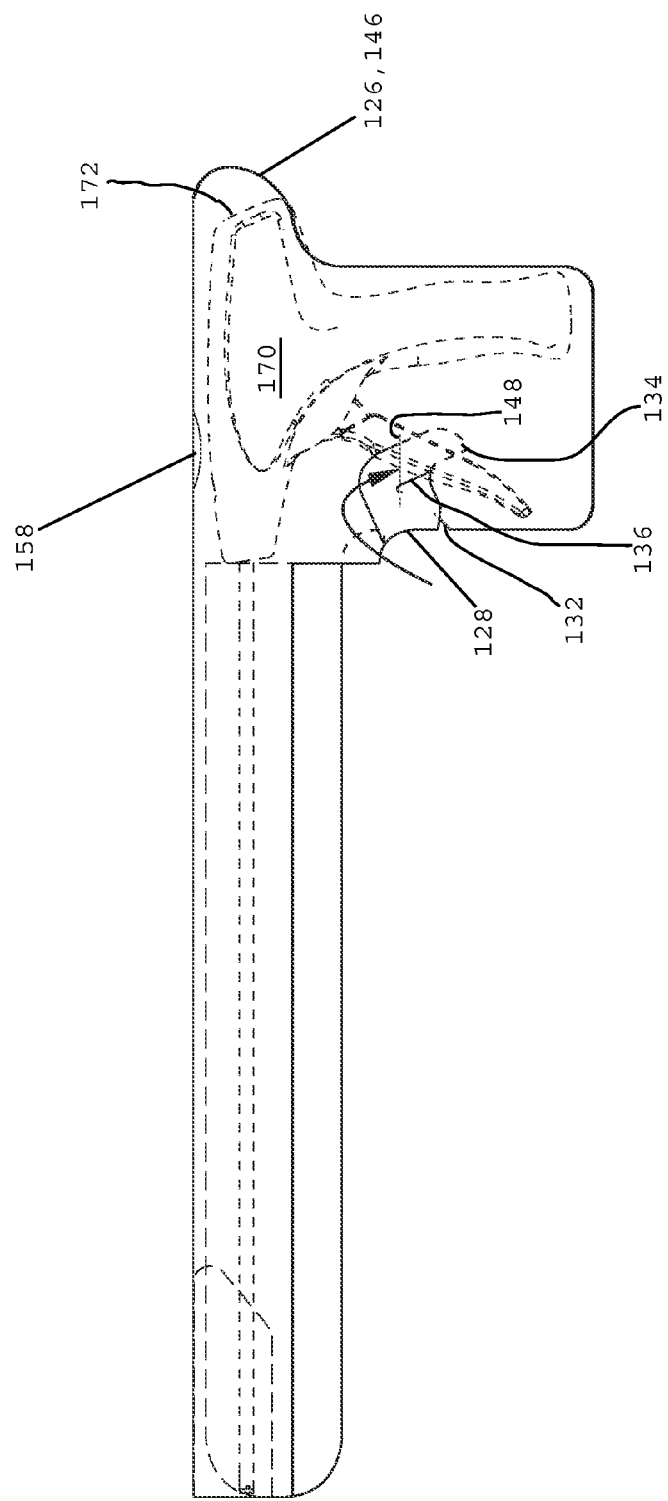

Referring to FIGS. 6 and 7, in one embodiment, after the second handle cover section 142 is folded over the first handle cover section 122 (FIG. 5), the hook 134 of the stop tab 128 is desirably inserted into the locking slot 148 formed in the second handle cover section 142 for holding respective distal edges of the first and second handle cover sections together. The angled cut line 132 enables the stop tab 128 to be wrapped around the distal edges of the first and second handle covers without tearing the blank 110. The vertical cut line 136 adjacent the hooked end 134 preferably enables the hooked end to be fully inserted into the locking slot 148 for reliable securing the stop tab 128 within the locking slot 148.

Figure 8:
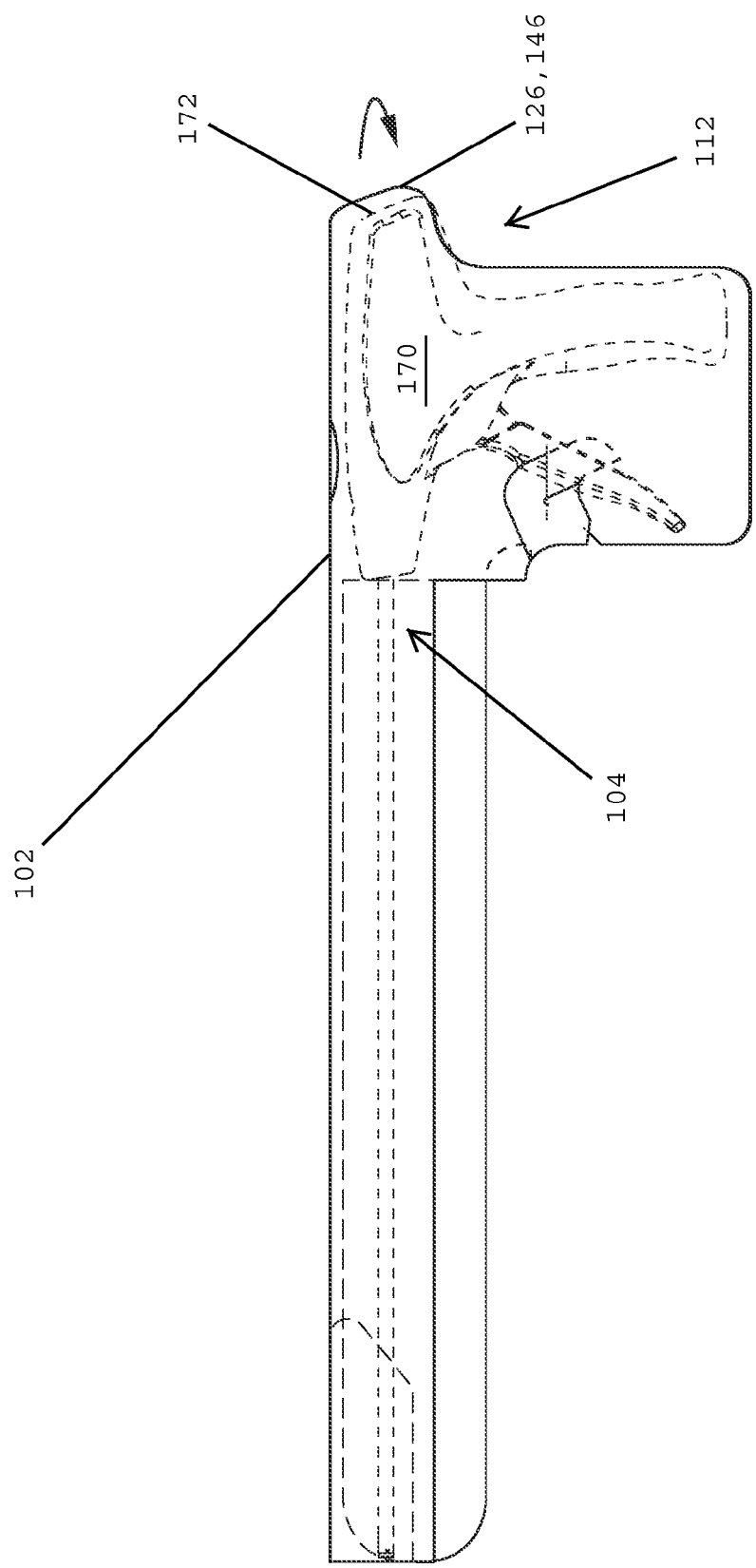

Referring to FIGS. 7 and 8, in one embodiment, the first and second proximal end tabs 126, 146 may be folded over the proximal end 172 of the handle 170. The first and second proximal tabs 126, 146 preferably cover the proximal end 172 of the handle 170 for protecting the proximal end of the medical device and/or preventing movement or shifting of the medical device 104 toward the proximal end 112 of the holster 102.

Figure 9:
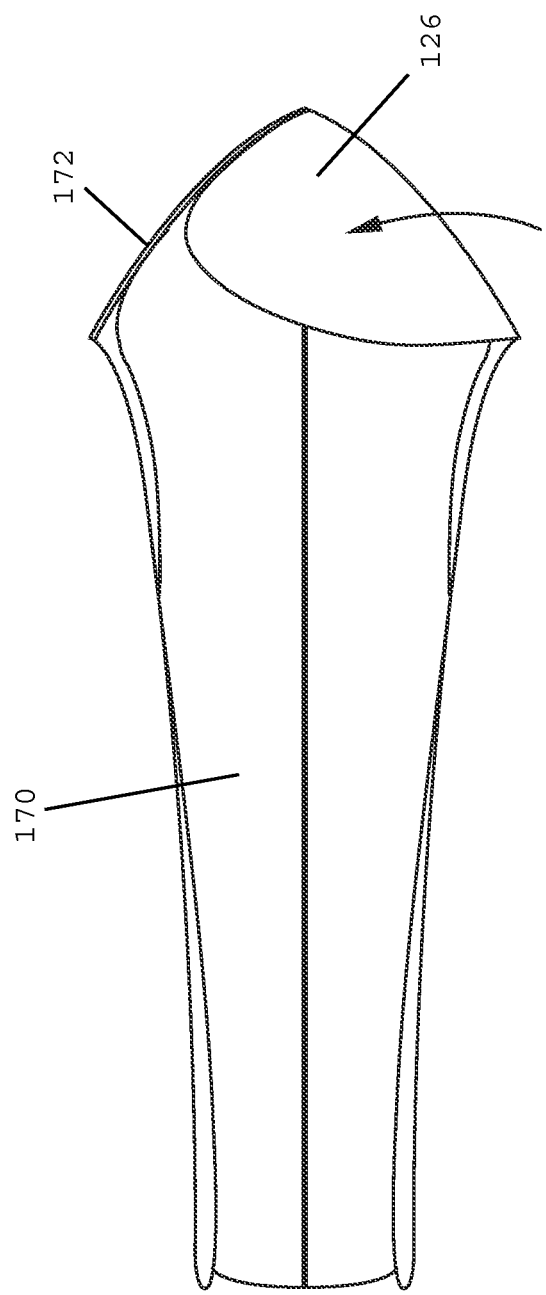
Figure 10:
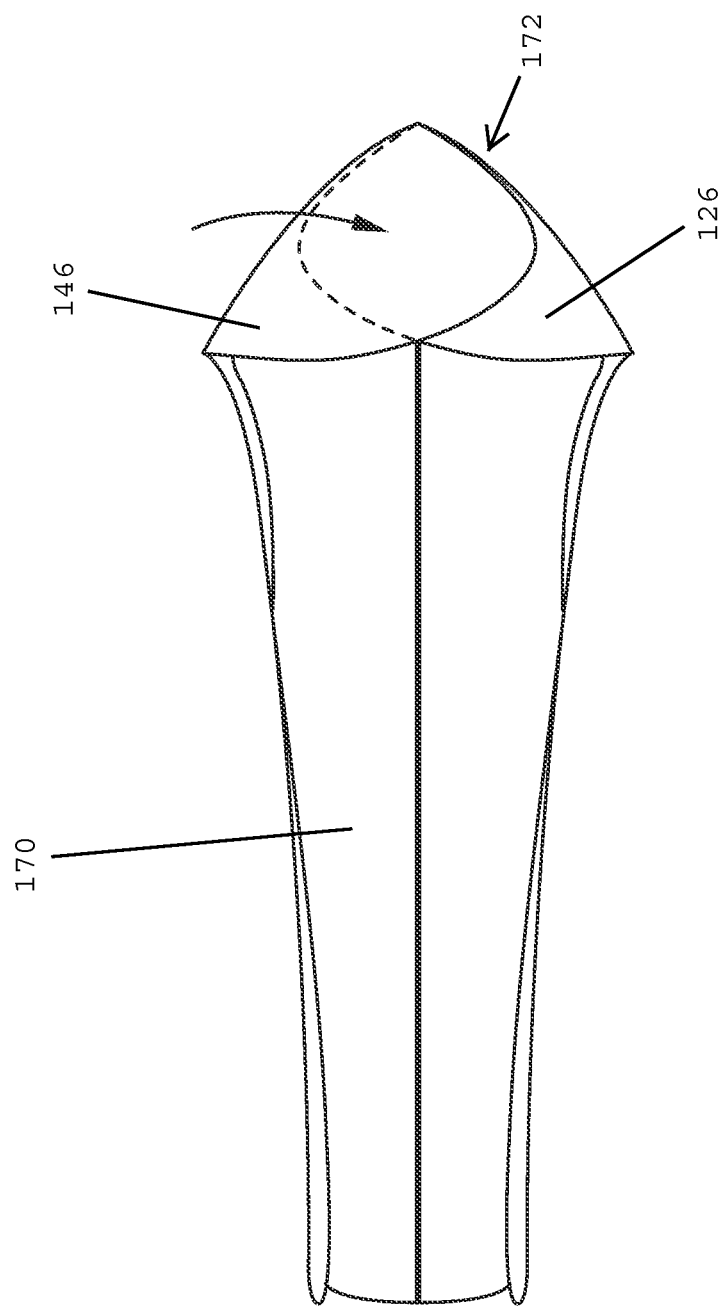

Referring to FIG. 9, in one embodiment, the proximal end 172 of the handle 170 is covered by folding the first proximal end tab 126 over the proximal end of the handle. Referring to FIG. 10, in one embodiment, the second proximal end tab 146 is folded over the first proximal end tab 126 and the proximal end 172 of the handle 170 for completely covering the proximal end 172 of the handle 170.

Figure 11:
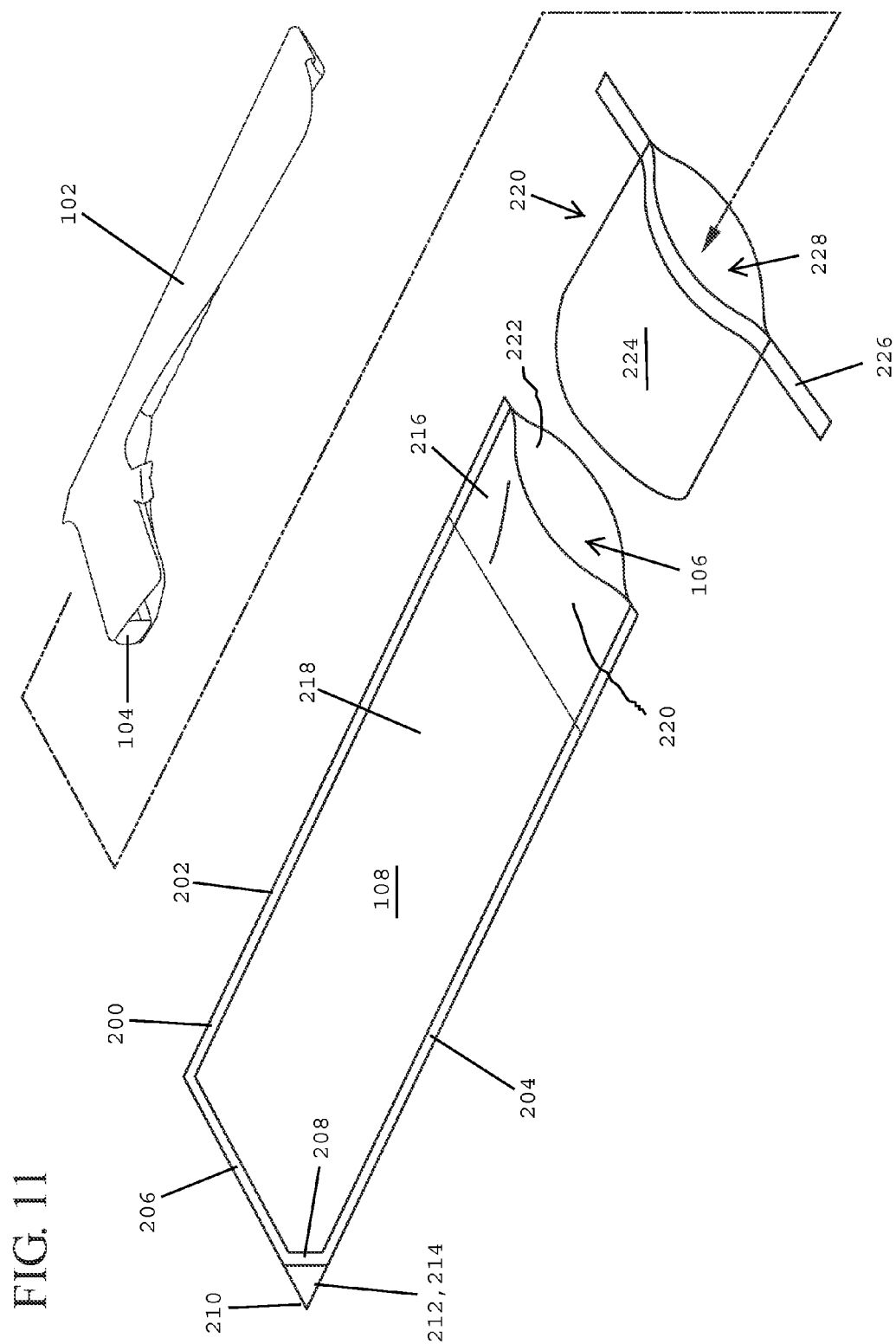
FIGS. 11-14 show a method of inserting the holster and medical device of FIG. 8 inside the pouch of FIG. 1, in accordance with one embodiment of the present invention.

Referring to FIG. 11, in one embodiment, after the medical device 104 has been wrapped inside the holster 102, the holster and the medical device may be inserted into the opening 106 at an unsealed end of the pouch 108. In one embodiment, the pouch 108 preferably has a seal 200 that extends along three sides of the pouch including a bottom sealed edge 202, a top sealed edge 204 and a first side sealed edge 206. The bottom and top sealed edges 202, 204 have proximal ends that extend to the opening 106. The seal 200 includes a diagonally-extending sealed section 208 that extends between the first side sealed edge 206 and the top sealed edge 204. The diagonally-extending sealed edge 208 is spaced from a corner 210 of the pouch 108. The pouch 108 preferably includes a pair of tabs 212, 214 located in the corner 210 that may be peeled away from one another for breaking the seal 200 and opening the pouch 108, as will be described in more detail below.

In one embodiment, the pouch includes a first sealable section 216 that is used for sterilizing the medical device and a second sealable section 218 that is used for forming a final seal on the pouch after a sterilization and drying process has been completed. The first section 216 of the pouch 108 preferably includes a first foil sheet 220 and an opposing Tyvek® sheet 222. As is well known to those skilled in the art, the Tyvek® sheet is porous for enabling a sterilization process to be preformed therethrough. The second section 218 preferably includes opposing foil sheets.

In one embodiment, an insertion guide 220 is used for inserting the holster 102 and the medical device 104 into the opening 106 of the pouch 108. The insertion guide preferably includes a tubular section 224 that is insertable into the opening 106 of the pouch 108 and a stop flange 226 that extends outside the perimeter of the tubular section 224. The tubular section 224 preferably includes an insertion guide opening 228 that extends along the length of the insertion guide 220 for passing the holster 102 and the wrapped medical device 104 therethrough.

Figure 12:
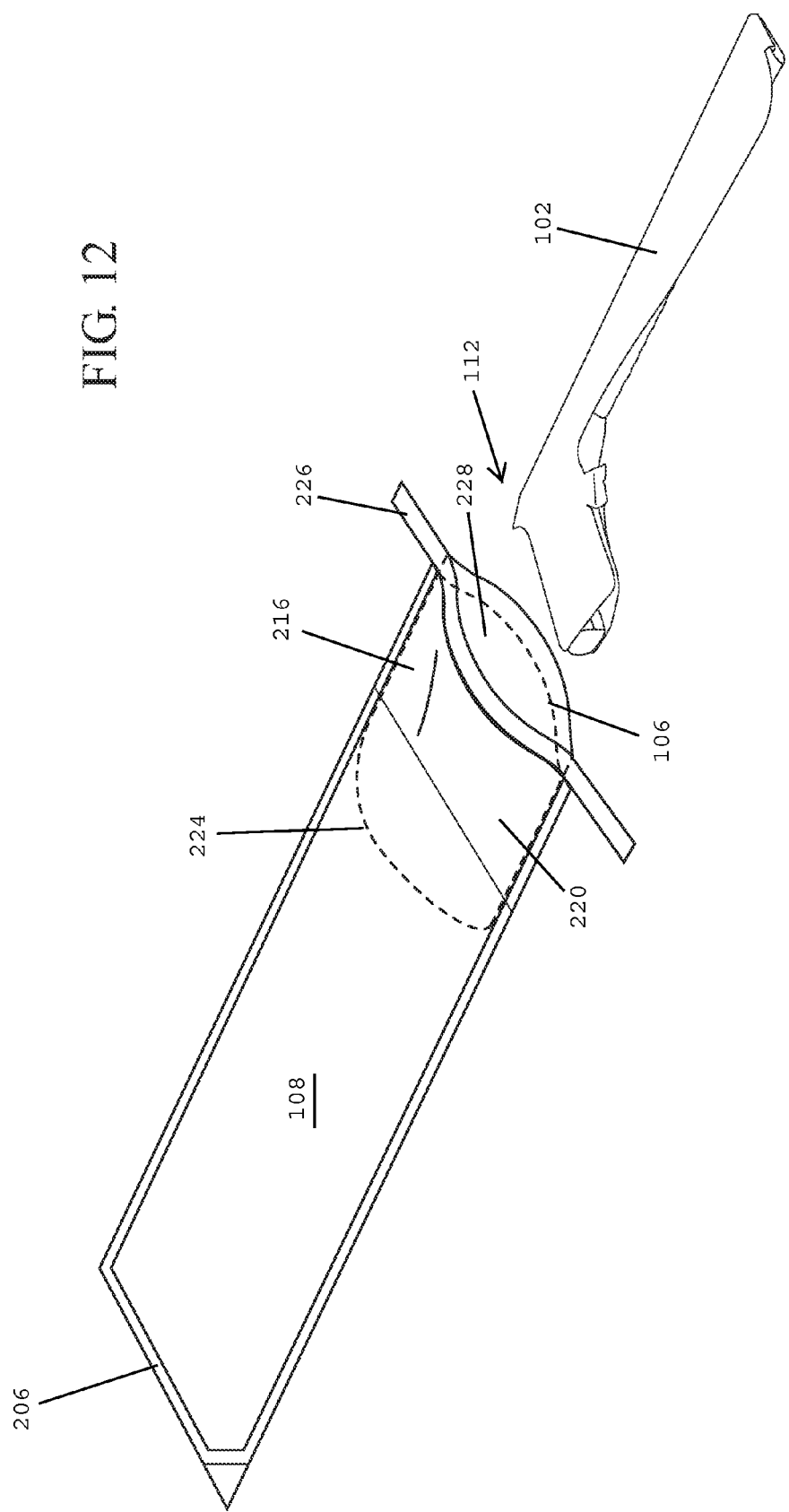

Referring to FIG. 12, in one embodiment, the tubular section 224 of the insertion guide 220 is inserted into the pouch opening 106 until the stop flange 226 abuts against the side edge of the first section 216 of the pouch 108.

Figure 13:
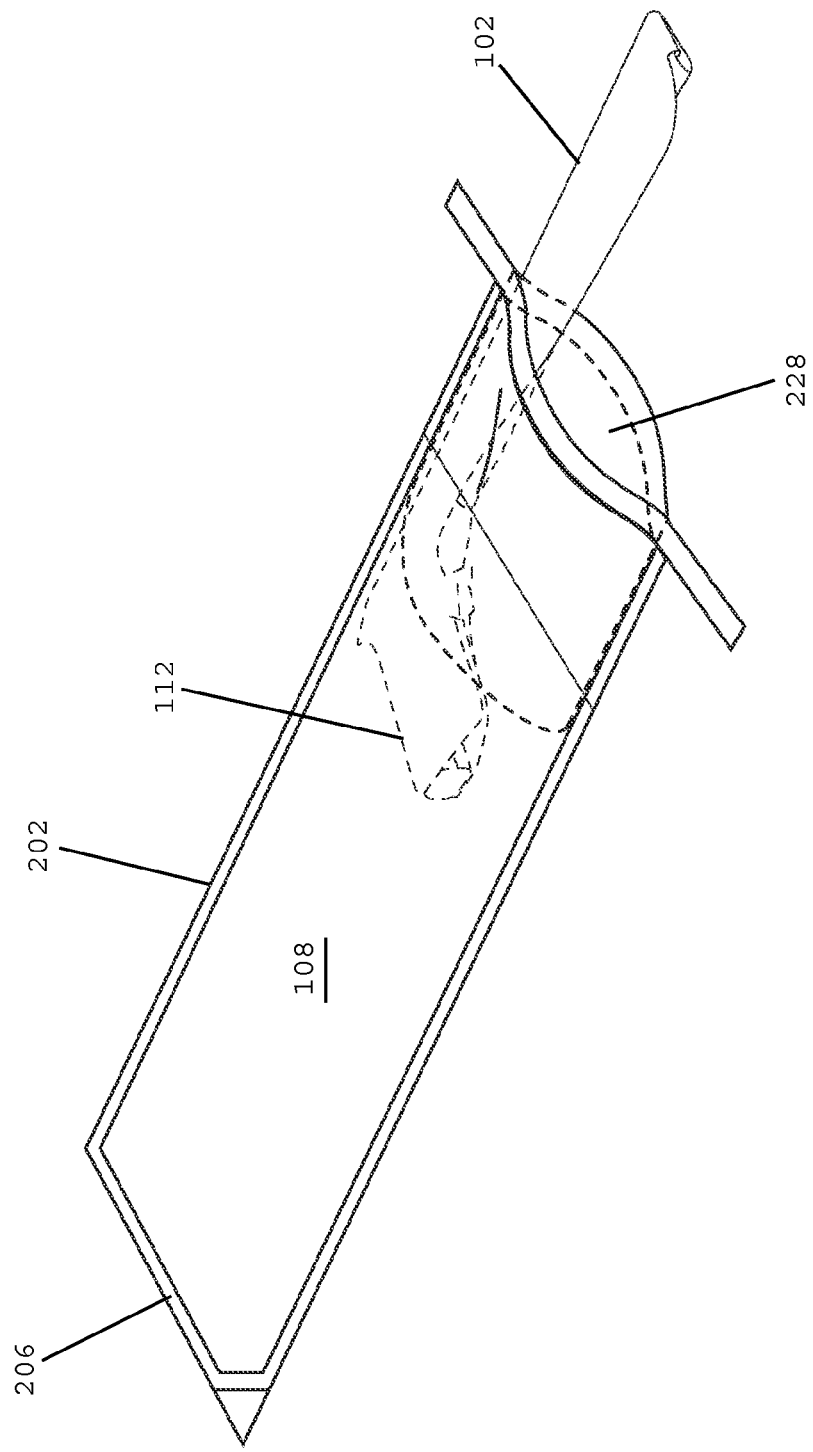

Referring to FIGS. 12 and 13, in one embodiment, the proximal end 112 of the holster 102 and the handle end of the medical device are inserted through the insertion guide opening 228, through the pouch opening 106 and advanced toward the first side sealed edge 206 of the pouch 108. The section of the holster 102 surrounding the elongated shaft is preferably positioned adjacent the bottom sealed edge 202 of the pouch 108 to provide a bottom-loaded package.

Figure 14:
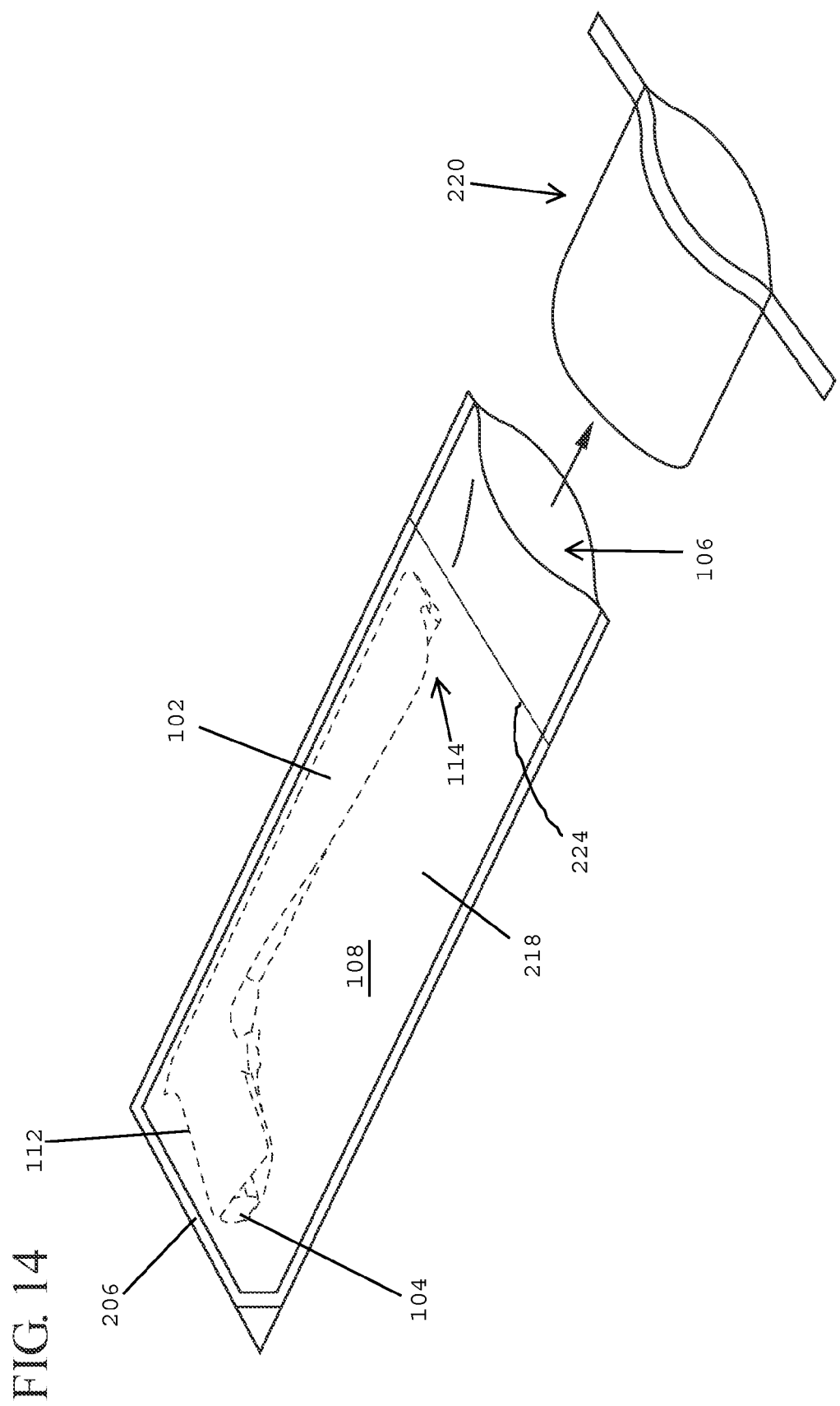

Referring to FIG. 14, in one embodiment, the holster 102 and the wrapped medical device 104 are preferably advanced toward the first side sealed edge 206 of the pouch 108 until the distal end 114 of the holster 102 is positioned inside the final seal line 224 of the second section 218 of the pouch 108. After the holster and the medical device have been properly positioned within the pouch, the insertion guide 220 may be removed from the opening 106 of the pouch 108.

Figure 15:
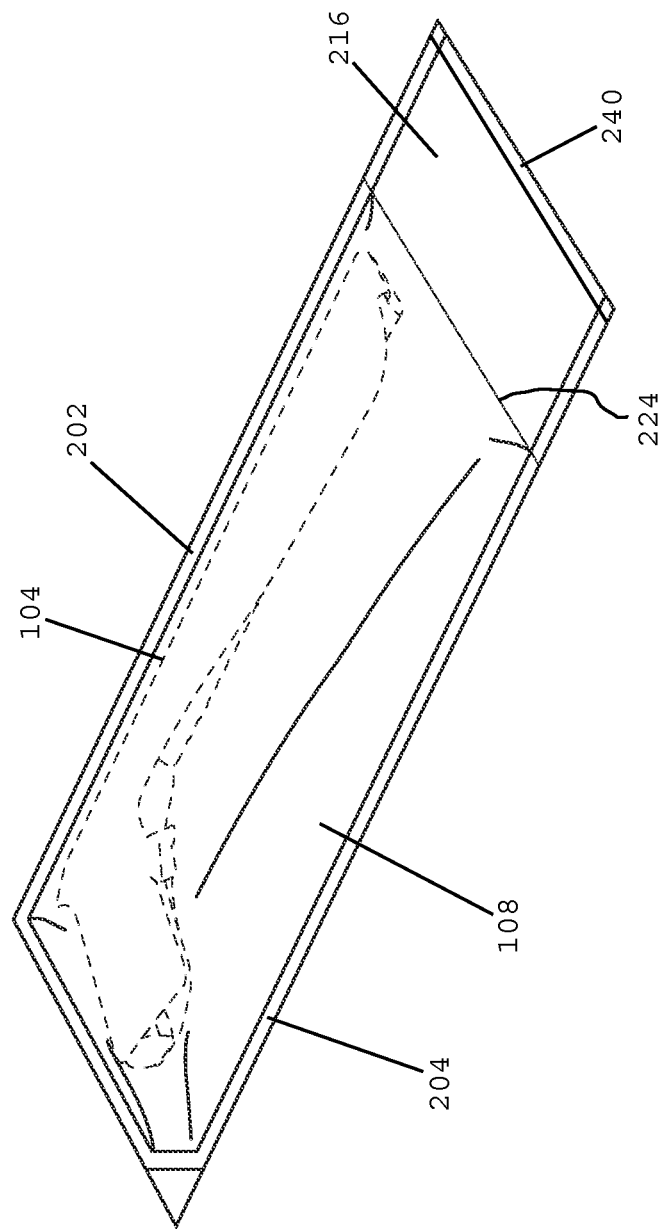
FIGS. 15 and 16 show a method of sterilizing and sealing the holster and medical device of FIG. 14 inside the pouch of FIG. 1, in accordance with one embodiment of the present invention.

Referring to FIG. 15, in one embodiment, a temporary seal 240 is preferably formed at the open side edge of the first section 216 of the pouch 108 for sealing together the foil sheet 220 and the Tyvek® sheet 222 (FIG. 11). After the temporary seal 240 is formed, the first section 216 and the second section 218 of the pouch 108 remain in fluid communication with one another.

In one embodiment, the pouch 108 is preferably oriented in an upright configuration so that the bottom sealed edge 202 defines a bottom of the package and the top sealed edge 204 defines a top of the package, with the elongated shaft of the medical device and the tubular member of the holster 102 extending along the bottom sealed edge of the pouch for forming a bottom-loaded package. The pouch 108 may be stored in a tray in the upright configuration. The sealed pouch 108 and the contents therein may be subjected to a sterilization process whereby the porous Tyvek® sheet facilitates the sterilization procedure. After sterilization, the sealed pouch 108 may be vacuumed dried and filled with nitrogen.

Figure 16:
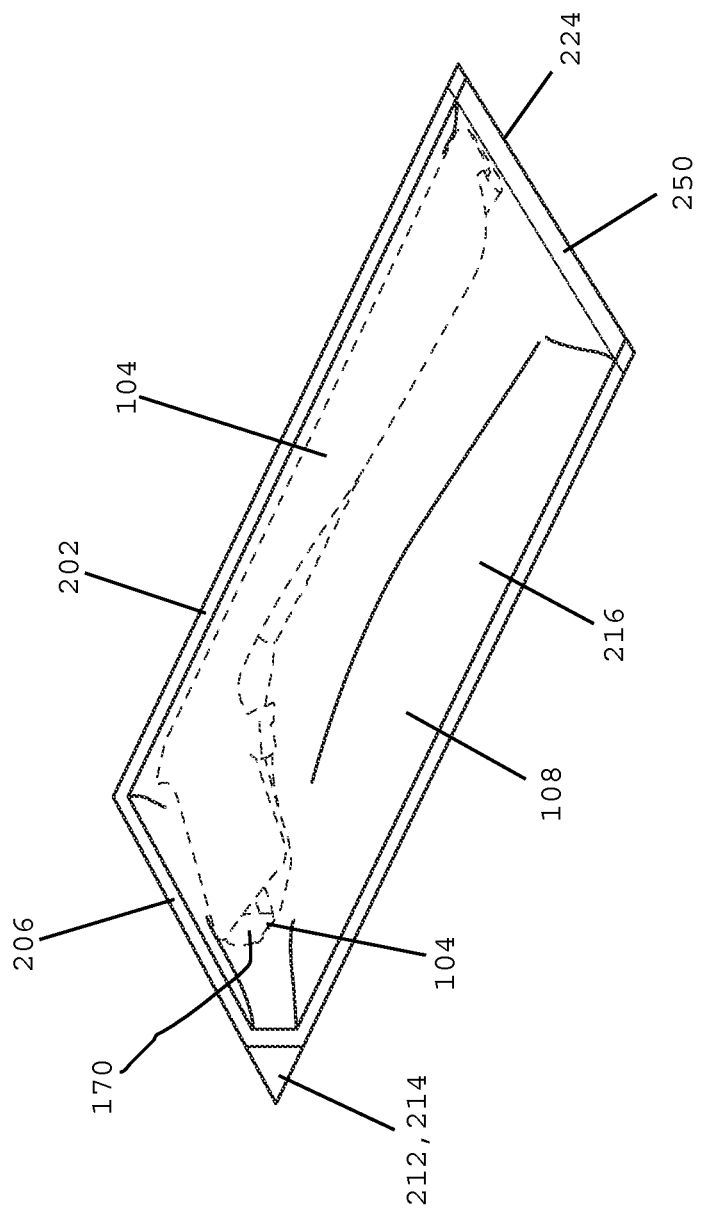

Referring to FIGS. 15 and 16, after the sealed pouch 106 is filled with nitrogen, a final seal 250 is preferably formed inside the final seal line 224 for sealing the two opposing foil panels together. After the final seal 250 is formed, the first section 216 of the pouch 108 including the Tyvek® sheet may be detached from the pouch 108 to provide a final sealed package having the shape and size shown in FIG. 16. After the holster 102 and the wrapped medical device 102 have been sealed within the pouch 108, the handle 170 of the medical device is preferably located adjacent the first side sealed edge 206 and the elongated shaft of the medical device preferably extends adjacent the bottom sealed edge 202 to provide a bottom-loaded package. The final seal 250 preferably extends transversely relative to the distal end of the elongated shaft of the medical device 104.

Positioning the distal end of the elongated shaft of the medical device adjacent the final seal 250 enables a smaller pouch to be used because the elongated shaft is thinner than the handle end of the medical device so that the flat seal area distance from the distal tip of the medical device (a three dimensional component) to the final seal (a two dimensional component) is minimized. If the larger three dimensional handle was nearest to the final seal, the flat seal area would have to be located at a greater distance from the medical device which would require a longer pouch.

Figure 17:
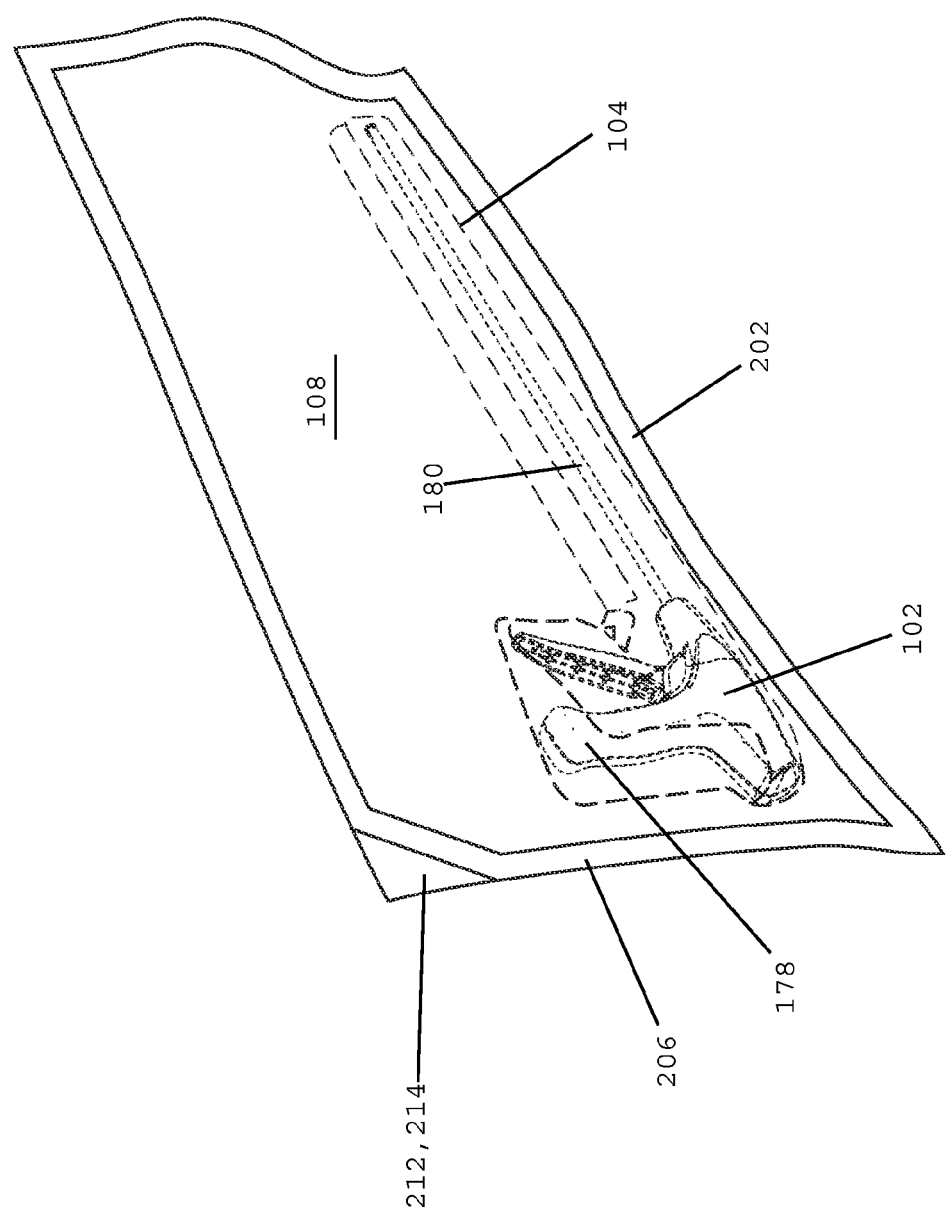
FIGS. 17-21 show a method of opening a pouch for removing a medical device from a holster and the pouch, in accordance with one embodiment of the present invention.

Referring to FIGS. 16 and 17, in one embodiment, the holster 102 and the medical device 102 are positioned within the sealed pouch 108 so that the hand grip 178 of the handle 170 extends along the first side sealed edge 206 of the pouch 108 and the elongated shaft 180 of the medical device extends along the bottom sealed edge 202 of the pouch. The first and second pull tabs 212, 214 are desirably located adjacent a bottom of the hand grip 178 of the handle of the medical device. The sealed pouch 108 is bottom-loaded so that the elongated shaft 180 of the medical device 104 extends along the bottom sealed edge 202 thereof. The sealed pouch 108 is preferably packaged, sterilized, sealed and stored in the upright vertical configuration shown in FIG. 17 with the bottom sealed edge 202 extending along the bottom of the pouch. Providing a bottom-loaded package minimizes shifting of the holster 104 and the wrapped medical device 102 within the sealed pouch 108 so as to minimize the need for using fastening elements (e.g. staples, tacks, adhesive) for attaching the holster 104 to the pouch to prevent the holster and the medical device from shifting within the sealed pouch 108.

Figure 18:
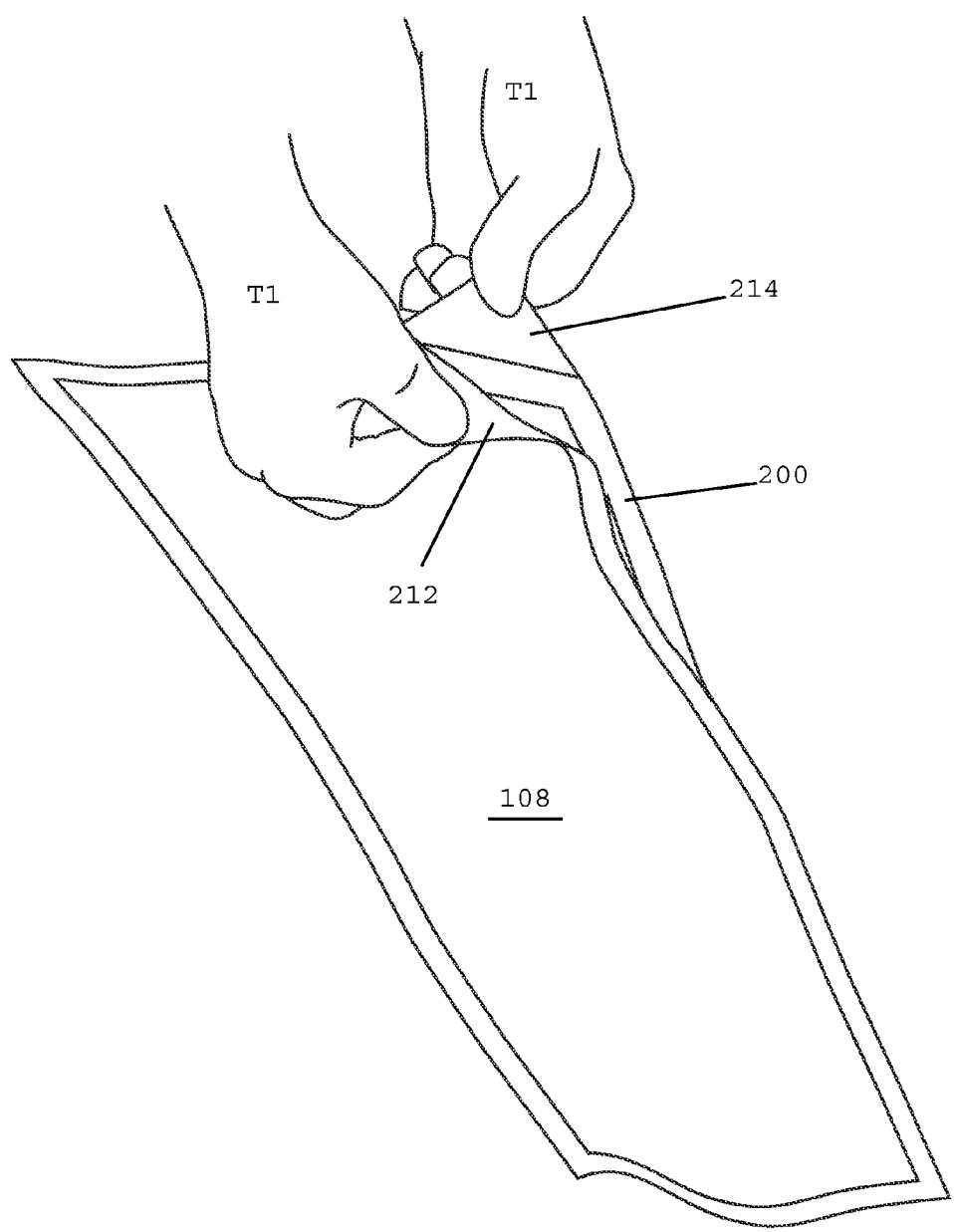
Figure 19:
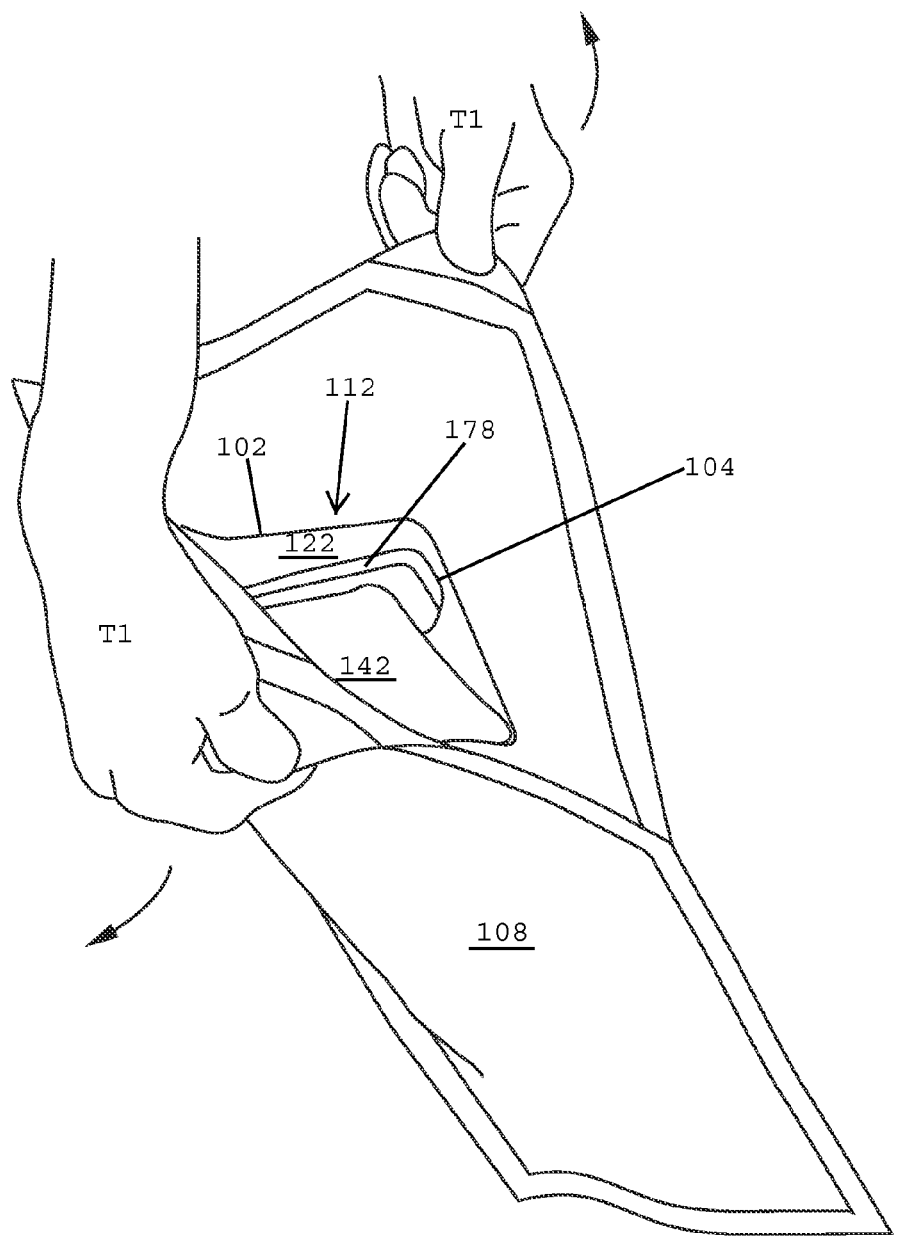

Referring to FIG. 18, in one embodiment, during a medical procedure, a first surgical technician T1 in a non-sterile environment may grasp the first and second pull tabs 212, 214 for breaking the seal 200 and opening the pouch 108. FIG. 19 shows further opening of the sealed pouch 108 for accessing the medical device 104 at the proximal end 112 of the holster 102. As the foil sheets of the pouch 108 are peeled away from one another, the first and second handle cover sections 122, 142 desirably spring away from one another, due, in part, to the oval-shaped element 158 located along the central fold line 116 (FIG. 2), for providing access to the hand grip 178 of the handle 170 (FIG. 3). Although the present invention is not limited by any particular theory of operation, it is believed that the ability of the proximal end of the holster to spring open makes it easier for a surgical technician to reach into the pouch and grasp the medical device for withdrawal while maintaining the sterile condition of the medical device. Moreover, the position of the oval-shaped element 158 relative to the stop tab 128 (see FIGS. 2 and 7) also provides the springing open action.

The gap between the first and second handle cover sections 122, 142 defines a holster opening into which a surgical technician may reach for grasping the medical device 104. As shown in FIG. 19, the distal edges of the first and second handle cover sections are closer together than the proximal edges of the first and second handle cover sections. This wedge shaped orientation of the first and second handle cover sections is the result of the stop tab 128 coupling the proximal edges together as shown in FIG. 7.

Figure 20:
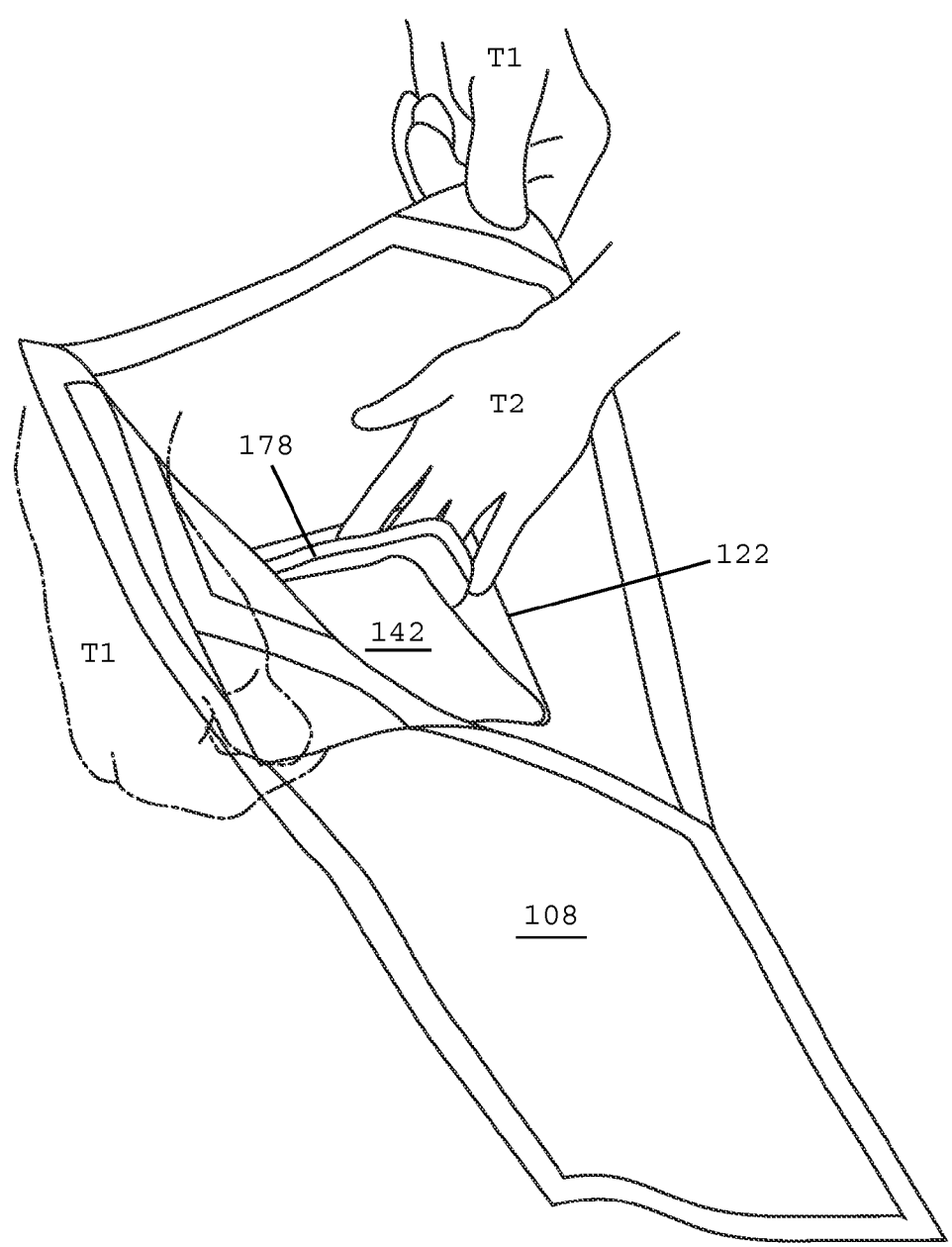
Figure 21:
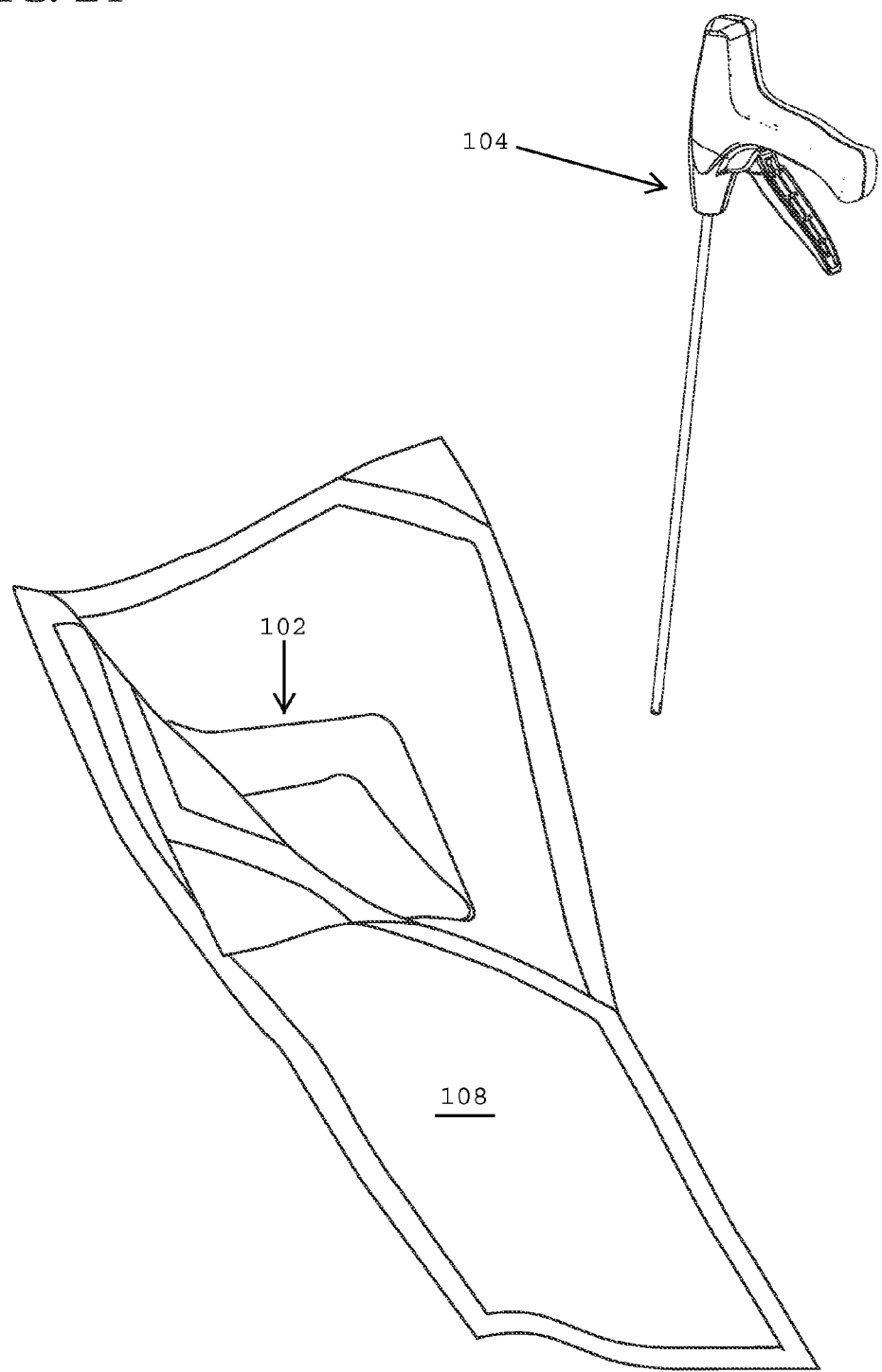

Referring to FIG. 20, in one embodiment as the first surgical technician T1 keeps the pouch 108 open, a second surgical technician T2, in a sterile environment, may reach through the opening of the pouch 108 and into the holster opening between the first and second handle cover sections 122, 142 for grasping the hand grip 178 of the medical device. Referring to FIG. 21, the medical device 104 is preferably drawn from the holster opening and the pouch 108 for use during a medical procedure. The transfer of the medical device 104 from the pouch 108 to the sterile technician T2 (FIG. 20) preferably takes place during an aseptic transfer whereby the medical device is delivered to a sterile environment (e.g., an operating room) without being contaminated with bacteria or other microorganisms.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention

What is claimed is:

1. A package for a medical device comprising:
   a medical device including a handle and an elongated shaft projecting from said handle;
   a holster for holding said medical device, said holster including a tubular member that extends to a distal end thereof for receiving said elongated shaft and a handle cover located at a proximal end thereof that receives said handle, said handle cover having a holster opening for accessing said handle to draw said medical device from said proximal end of said holster, wherein said holster includes a foldable blank having an oval-shaped opening located along a center fold line of said foldable blank, and disposed between distal edges of first and second handle cover sections and said proximal end of said holster; and
   a pouch having a sealed area bounded by a top sealed edge, a bottom sealed edge, and a pair of side sealed edges extending between said top and bottom sealed edges, said pouch including an opening tab located only in a single corner of said pouch and spaced from said bottom sealed edge, wherein said medical device and said holster are disposed within said enclosed area of said sealed pouch with said elongated shaft of said medical device extending along said bottom sealed edge and said holster opening being located adjacent said opening tab.

2. The package as claimed in claim 1, wherein said handle and said handle cover extend away from said bottom sealed edge toward said opening tab.

3. The package as claimed in claim 2, wherein said opening tab is closer to said holster opening than said distal end of said holster, and said distal end of said holster is diagonally opposite said opening tab.

4. The package as claimed in claim 1, wherein said holster comprises paper adapted to absorb moisture inside said pouch.

5. The package as claimed in claim 4, wherein said holster comprises solid bleach sulfate material.

6. The package as claimed in claim 1, wherein said pouch comprises a foil pouch including first and second foil sheets that are sealed together by a continuous seal including said upper sealed edge, said bottom sealed edge and said pair of side sealed edges.

7. The package as claimed in claim 6, wherein said opening tab comprises a first pull tab connected with said first foil sheet and a second pull tab connected with said second foil sheet.

8. The package as claimed in claim 7, wherein said first and second pull tabs are peelable away from one another for breaking said continuous seal to open said pouch for accessing said medical device through said holster opening.

9. The package as claimed in claim 1, wherein said pouch has a rectangular shape and said top and bottom sealed edges extend along the length of said sealed pouch.

10. The package as claimed in claim 9, wherein said opening tab is spaced from said bottom sealed edge and is located in a first corner of said pouch that is diagonally opposite from a second corner of said pouch that is adjacent a distal end of said elongated shaft.

11. The package as claimed in claim 1, wherein said holster includes said foldable blank comprising:
   a first blank half including said first handle cover section adjacent said proximal end of said holster and a first shaft cover extending between said first handle cover section and said distal end of said holster;
   a second blank half including said second handle cover section adjacent said proximal end of said holster and a second shaft cover extending between said second handle cover section and said distal end of said holster, wherein said second blank half is foldable along the center fold line for covering said first blank half;
   a stop tab coupling the distal edges of said first and second handle cover sections together for limiting distal movement of said handle relative to said first and second handle cover sections.

12. A package for a medical device comprising:
   a medical device including a handle and an elongated shaft projecting from said handle;
   a holster for holding said medical device, said holster including a tubular member that extends to a distal end thereof for receiving said elongated shaft and a handle cover located at a proximal end thereof that receives said handle, said handle cover having a holster opening for accessing said handle to draw said medical device from said proximal end of said holster;
   a pouch having a sealed area bounded by a top sealed edge, a bottom sealed edge, and a pair of side sealed edges extending between said top and bottom sealed edges, said pouch including at least one opening tab spaced from said bottom sealed edge, wherein said medical device and said holster are disposed within said enclosed area of said sealed pouch with said elongated shaft of said medical device extending along said bottom sealed edge and said holster opening being located adjacent said at least one opening tab, wherein said holster includes a foldable blank comprising
   a first blank half, a second blank half, and a center fold line extending between said first and second blank halves;
   said first blank half including a first handle cover section adjacent said proximal end of said holster and a first shaft cover extending between said first handle cover section and said distal end of said holster;
   said second blank half including a second handle cover section adjacent said proximal end of said holster and a second shaft cover extending between said second handle cover section and said distal end of said holster, wherein said second blank half is foldable along said center fold line for covering said first blank half;
   a stop tab projecting from a distal edge of said first handle cover section; and
   a locking slit formed in said second handle cover section, wherein said stop tab is adapted to engage said locking slit for coupling distal edges of said first and second handle cover sections together.

13. The package as claimed in claim 12, wherein said stop tab is adapted to stop movement of said medical device toward said distal end of said holster when said medical device is inserted into said holster.

14. The package as claimed in claim 12, wherein said holster further comprises a distal tab projecting from a distal end of said first shaft cover, said distal tab being foldable over a distal end of said shaft of said medical device when said medical device is positioned over said blank.

15. The package as claimed in claim 14, wherein said second shaft cover comprises a score line that extends along the length of said second shaft cover for bisecting said second shaft cover into a first foldable part and a second foldable part, and a cut line that intersects with a proximal end of said score line for enabling said first foldable part to be folded over said second foldable part along said score line.

16. The package as claimed in claim 15, wherein said first foldable part is foldable over said second foldable part which, in turn, is foldable over said first shaft cover for forming said tubular member.

17. The package as claimed in claim 16, wherein said distal tab is positionable between said first foldable part and said second foldable part for covering a distal end of said tubular member and a distal end of said medical device shaft.

18. A package for a medical device comprising:
   a medical device including a handle at a proximal end and an elongated shaft that extends toward a distal end of said medical device;
   a holster adapted to receive and hold said medical device, said holster including a tubular member that receives said elongated shaft and a handle cover that at least partially covers said handle, said handle cover having a holster opening for accessing said handle and drawing said medical device from said holster, wherein said holster includes a foldable blank having an oval-shaped opening located along a center fold line of said foldable blank, and disposed between distal edges of first and second handle cover sections of said foldable blank and a proximal end of said holster;
   a rectangular shaped sealed pouch having a bottom sealed edge, a top sealed edge, a pair of side sealed edges that extend between said top and bottom sealed edges, and an opening tab located only in a single corner of said pouch and spaced from said bottom sealed edge, wherein said medical device and said holster containing said medical device are positioned within an enclosed area of said sealed pouch so that said elongated shaft extends along said bottom sealed edge and said holster opening is adjacent said opening tab, and wherein said opening tab is spaced from said bottom sealed edge and is diagonally opposite from a distal end of said medical device shaft.

19. The package as claimed in claim 18, wherein said holster includes said foldable blank comprising:
   a first blank half including said first handle cover section adjacent said proximal end of said holster and a first shaft cover extending between said first handle cover section and said distal end of said holster;
   a second blank half including said second handle cover section adjacent said proximal end of said holster and a second shaft cover extending between said second handle cover section and said distal end of said holster, wherein said second blank half is foldable along the center fold line for covering said first blank half; and
   a stop tab coupling the distal edges of said first and second handle cover sections together for limiting distal movement of said handle relative to said first and second handle cover sections.

\* \* \* \* \*